United States Patent
Arimoto et al.

(10) Patent No.: US 10,068,679 B2
(45) Date of Patent: Sep. 4, 2018

(54) SCINTILLATOR PANEL AND PRODUCTION METHOD THEREOF

(71) Applicant: Konica Minolta, Inc., Tokyo (JP)

(72) Inventors: Tadashi Arimoto, Hino (JP); Hiromichi Shindou, Hachioji (JP); Atsushi Hasegawa, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 14/900,855

(22) PCT Filed: Jul. 3, 2014

(86) PCT No.: PCT/JP2014/067839
§ 371 (c)(1),
(2) Date: Dec. 22, 2015

(87) PCT Pub. No.: WO2015/002281
PCT Pub. Date: Jan. 8, 2015

(65) Prior Publication Data
US 2016/0155526 A1    Jun. 2, 2016

(30) Foreign Application Priority Data

Jul. 4, 2013 (JP) .................. 2013-140563

(51) Int. Cl.
*G01T 1/00* (2006.01)
*G21K 4/00* (2006.01)
(Continued)

(52) U.S. Cl.
CPC .............. *G21K 4/00* (2013.01); *C09K 11/628* (2013.01); *G01T 1/20* (2013.01); *A61B 6/4233* (2013.01);
(Continued)

(58) Field of Classification Search
CPC ........ G01T 1/20; G21K 2004/06; G21K 4/00; G21K 2004/04; A61B 6/4233; A61B 6/4283; C09K 11/55; C09K 11/628
(Continued)

(56) References Cited

U.S. PATENT DOCUMENTS 8,106,363 B2 *   1/2012   Yip ..................... G01T 1/2018
                                                             250/370.09
8,822,941 B2 *   9/2014   Ikeda .................... G01T 1/2006
                                                             250/361 R
(Continued)

FOREIGN PATENT DOCUMENTS

JP          H05312961 A       11/1993
JP          H06331749 A       12/1994
(Continued)

OTHER PUBLICATIONS

International Search Report: International Application No. PCT/JP2014/067839 dated Aug. 19, 2014; total of 5 pages.
(Continued)

*Primary Examiner* — Taeho Jo
(74) *Attorney, Agent, or Firm* — Lucas & Mercanti, LLP

(57) ABSTRACT

Provided is a scintillator panel realizing reduced image unevenness and the like by virtue of having a cushioning layer between a support and a phosphor. The cushioning layer absorbs irregularities on the phosphor layer when the scintillator panel is compression bonded to a planar light-receiving element and thereby allows the phosphor layer to be in contact with the planar light-receiving element without any gaps in the interface. The scintillator panel includes, in the order named, a support, a cushioning layer disposed on a surface of the support, and a phosphor layer deposited on the surface of the cushioning layer, the cushioning layer having a specific thickness, the phosphor layer being configured to be placed into uniform contact with a surface of (Continued)

a planar light-receiving element when the phosphor layer is pressed against the planar light-receiving element by the application of a pressure from the support side.

10 Claims, 4 Drawing Sheets

(51) Int. Cl.
    *G01T 1/20*     (2006.01)
    *C09K 11/62*     (2006.01)
    *A61B 6/00*     (2006.01)

(52) U.S. Cl.
    CPC ........ *A61B 6/4283* (2013.01); *G21K 2004/04* (2013.01)

(58) Field of Classification Search
    USPC ...................................................... 250/448.1
    See application file for complete search history.

(56) References Cited

U.S. PATENT DOCUMENTS

| | | | |
|---|---|---|---|
| 2005/0040351 A1* | 2/2005 | Suzuki | C09K 11/671 250/580 |
| 2005/0194547 A1* | 9/2005 | Matsumoto | C09K 11/7733 250/484.4 |
| 2005/0199826 A1* | 9/2005 | Saito | G01T 1/2012 250/484.4 |
| 2005/0236582 A1* | 10/2005 | Nakatsu | C09K 11/778 250/484.4 |
| 2006/0065852 A1* | 3/2006 | Fukui | G03B 42/08 250/484.4 |
| 2006/0065863 A1* | 3/2006 | Takasu | C09K 11/7733 250/581 |
| 2006/0108683 A1* | 5/2006 | Takeda | H01L 27/14618 257/723 |
| 2006/0202134 A1* | 9/2006 | Fukui | C09K 11/671 250/484.4 |
| 2006/0255280 A1* | 11/2006 | Shibayama | H01L 27/14603 250/370.11 |
| 2008/0099687 A1* | 5/2008 | Shoji | G01T 1/2018 250/368 |
| 2008/0157003 A1* | 7/2008 | Hirai | C09K 11/7733 250/484.4 |
| 2008/0179533 A1* | 7/2008 | Nagata | G01T 1/2002 250/370.11 |
| 2008/0217550 A1* | 9/2008 | Shoji | G01T 1/2018 250/370.11 |
| 2009/0026383 A1* | 1/2009 | Kim | H01L 27/14676 250/370.11 |
| 2009/0261259 A1* | 10/2009 | Yip | G01T 1/2018 250/370.09 |
| 2010/0155612 A1* | 6/2010 | Takeda | G01T 1/00 250/370.08 |
| 2010/0243908 A1* | 9/2010 | Shoji | G01T 1/2002 250/370.11 |
| 2011/0133092 A1* | 6/2011 | Hansen | G01T 1/20 250/366 |
| 2011/0133093 A1* | 6/2011 | Jagannathan | G01T 1/20 250/366 |
| 2012/0211669 A1* | 8/2012 | Itaya | G01V 5/0025 250/458.1 |
| 2013/0019462 A1* | 1/2013 | Shoji | G01T 1/2018 29/595 |
| 2013/0048864 A1* | 2/2013 | Nakatsugawa | H01L 27/14618 250/366 |
| 2013/0068953 A1* | 3/2013 | Itaya | A61B 6/4208 250/368 |
| 2014/0014843 A1* | 1/2014 | Ikeda | G01T 1/2006 250/366 |

FOREIGN PATENT DOCUMENTS

| | | |
|---|---|---|
| JP | 2002116258 A | 4/2002 |
| JP | 2002236181 A | 8/2002 |
| JP | 3566926 B2 | 9/2004 |
| JP | 2008026013 A | 2/2008 |
| JP | WO2009037923 A1 * | 8/2008 |
| JP | 2013050364 A | 3/2013 |

OTHER PUBLICATIONS

John Rowlands, "Amorphous Semiconductor Usher in Digital X-ray Imaging", Physics Today, November issue, p. 24-30 (1997).
L. E. Antonuk, "development of a High-Resolution Active-Matrix Flat-Panel Imager with Enhanced Fill Factor", SPIE, 32, p. 2-14 (1997).
Written Opinion of he International Searching Authority; International Application No. PCT/JP2014/067839; filing date; Mar. 7, 2014; total of 7 pages.

* cited by examiner

[FIG. 1]
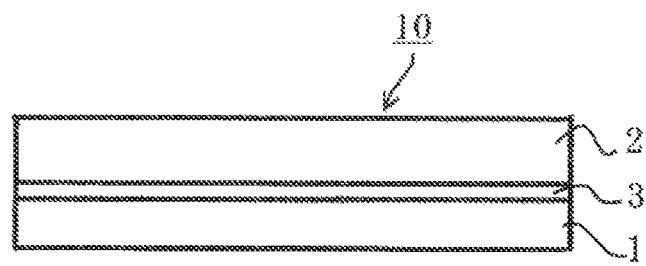
[FIG. 2]
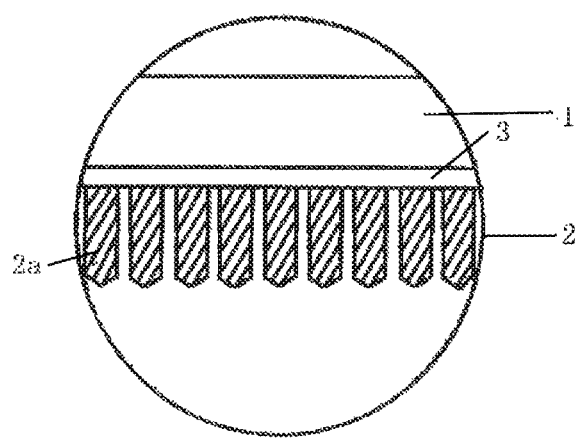

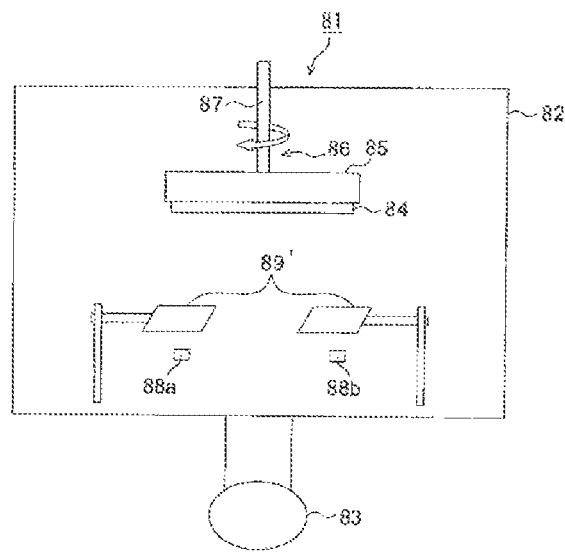
[FIG. 3]
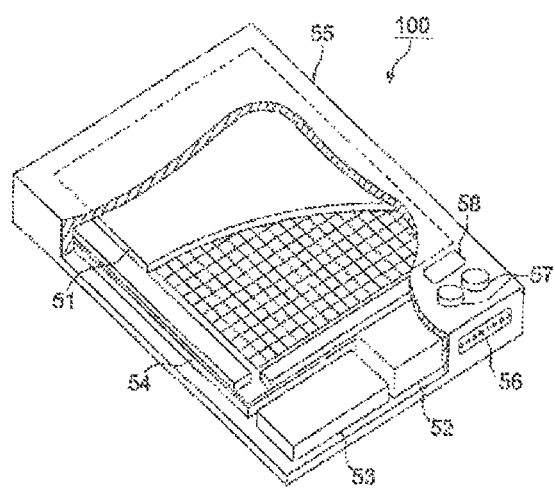
[FIG. 4]

[FIG. 5]
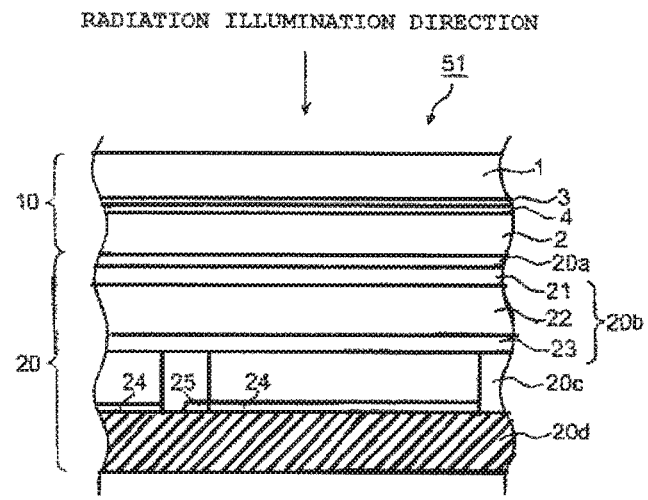
[FIG. 6]
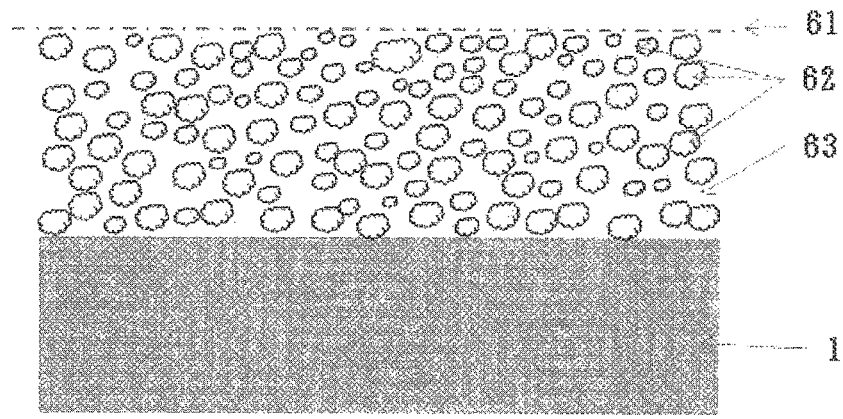

[FIG. 7]
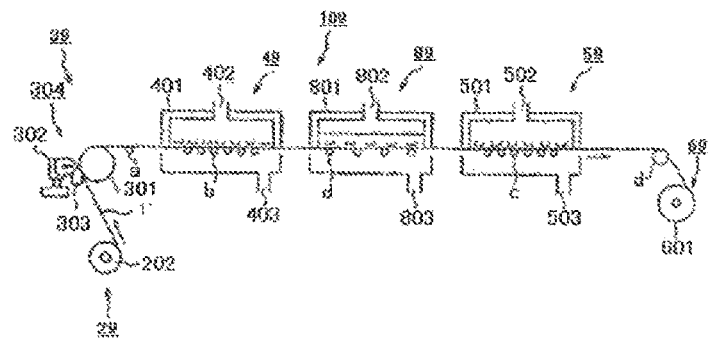
[FIG. 8]
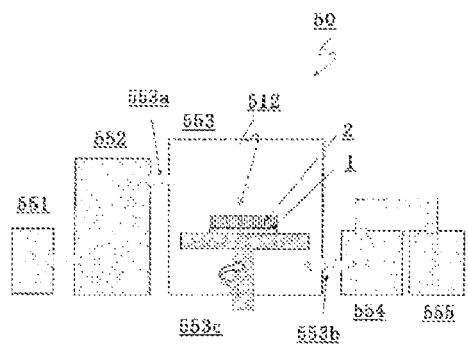
[FIG. 9]
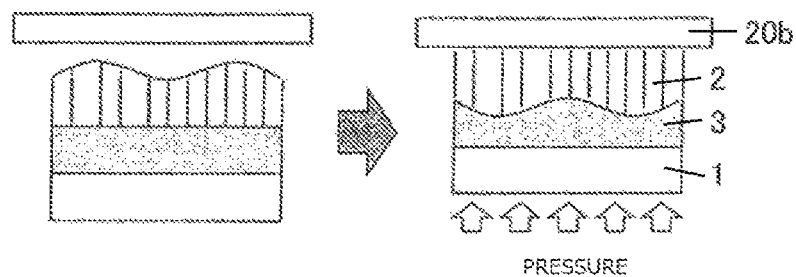
PRESSURE

SCINTILLATOR PANEL AND PRODUCTION METHOD THEREOF

CROSS REFERENCE TO RELATED APPLICATION

This Application is a 371 of PCT/JP2014/067839 filed on Jul. 3, 2014 which, in turn, claimed the priority of Japanese Patent Application No. JP2013-140563 filed on Jul. 4, 2013, both applications are incorporated herein by reference.

FIELD OF INVENTION

The present invention relates to scintillator panels used in the formation of radiographic images of subjects.

BACKGROUND ART

Radiographic images such as X-ray images have been widely used in medical diagnosis of disease conditions. In particular, radiographic images based on intensifying screen-film combinations have undergone enhancements in terms of sensitivity and image quality during a long history and consequently remain in use in the medical field worldwide as the imaging system with high reliability and excellent cost performance. However, this image information is analogue and thus cannot be processed freely or transmitted instantaneously in contrast to digital image information which has been developed currently.

Recently, digital radiographic image detectors such as computed radiography (CR) systems and flat panel detectors (FPDs) have come in use. These radiographic image detectors directly give digital radiographic images and allow the images to be directly displayed on displays such as cathode ray tube panels and liquid crystal panels.

Thus, there is no need for the images to be created on photographic films. Consequently, the digital X-ray image detectors have decreased a need for the image formation by silver halide photography and have significantly enhanced diagnostic convenience at hospitals and clinics.

The computed radiography (CR) is one of the digital X-ray image techniques currently used in medical practice. However, CR X-ray images are less sharp and are insufficient in spatial resolution as compared to screen film system images such as by silver halide photography, and the level of their image quality compares unfavorably to the quality level of screen film system images. Thus, new digital X-ray image techniques, for example, flat panel detectors (FPDs) involving a thin film transistor (TFT) have been developed (see, for example, Non Patent Literatures 1 and 2).

In principle, a FPD converts X-rays into visible light. For this purpose, a scintillator panel is used which has a phosphor (scintillator) layer made of an X-ray phosphor that, when illuminated with X-rays, convert the radiations into visible light that is emitted. In X-ray photography using a low-dose X-ray source, it is necessary to use a scintillator panel with high luminous efficiency (X-ray to visible light conversion) in order to enhance the ratio (the SN ratio) of signal to noise detected from the scintillator panel.

In the conventional production of scintillator panels by a gas-phase method, it is a general practice to form a phosphor layer on a rigid substrate made of such a material as aluminum or amorphous carbon, and cover the entire surface of the scintillator with a protective film (see, for example, Patent Literature 1). However, such scintillator panels having a phosphor layer on an inflexible and rigid substrate cause a difficulty in obtaining a uniform contact between the scintillator panel and a planar light-receiving element when they are bonded to each other. In detail, such a scintillator panel has irregularities ascribed to the unevenness of the substrate itself as well as to different heights of the columnar phosphor crystals in the phosphor layer, and the inflexible substrate significantly reflects the influence of such irregularities (a flexible substrate may cancel the irregularities by deformation) to make it difficult for the scintillator panel to be tightly and uniformly attached to a planar light-receiving element. To solve this problem, methods are proposed in which a spacer is used at the plane of contact between the scintillator panel and a planar light-receiving element (see, for example, Patent Literatures 2 and 3). However, this approach, which prioritizes the solution of problematic attachment between the scintillator panel and a planar light-receiving element over productivity, has a problem in that because the scintillator panel and the planar light-receiving element are spaced apart by a gap, the light produced in the phosphor layer of the scintillator panel is scattered in the gap to inevitably deteriorate the sharpness of the obtainable X-ray images. This problem has become more serious with the recent enlargement of flat panel detectors.

In order to solve the problems of loose attachment between scintillator panels and planar light-receiving elements as well as the problems associated with the use of spacers, methods have been generally adopted in which a phosphor layer is directly formed on an imaging element by deposition or in which a less sharp but flexible material such as a medical intensifying screen is used instead of a scintillator panel. Further, a method has been adopted in which a flexible protective layer made of such a material as a polyparaxylylene is used to protect layers such as phosphor layers in scintillator panels (see, for example, Patent Literature 4).

However, the substrates used in the above method are rigid materials such as aluminum and amorphous carbon. Even if the protective layer is formed with a thickness of about 10 μm on the phosphor layer or the substrate, the surface of the protective layer will show irregularities ascribed to the unevenness of the substrate itself as well as to different heights of the columnar phosphor crystals in the phosphor layer. Thus, even the adoption of such protective layers with the above thickness does not eliminate the influences of the irregularities on the substrates or the phosphor layers, and it remains difficult to achieve a uniform and close contact between the surface of the scintillator panel and the surface of a planar light-receiving element. On the other hand, increasing the thickness of the flexible protective layer increases the gap between the scintillator panel and a planar light-receiving element, resulting in a deterioration of the sharpness of the obtainable X-ray images.

Under such circumstances, there has been a demand for the development of radiographic flat panel detectors that have excellent luminous efficiency of scintillator panels and have small deteriorations in the sharpness of X-ray images due to factors such as the size of the gap between the scintillator panel and a planar light-receiving element.

CITATION LIST

Patent Literature

[Patent Literature 1] JP-B-3566926
[Patent Literature 2] JP-A-H05-312961
[Patent Literature 3] JP-A-H06-331749
[Patent Literature 4] JP-A-2002-116258

Non Patent Literature

[Non Patent Literature 1] John Rowlands, "Amorphous Semiconductor Usher in Digital X-ray Imaging", Physics Today, November issue, 24 (1997)

[Non Patent Literature 2] L. E. Antonuk, "Development of a High-Resolution Active-Matrix Flat-Panel Imager with Enhanced Fill Factor", SPIE, 32, 2 (1997)

SUMMARY OF THE INVENTION

Technical Problem

In the conventional production of scintillator panels by a gas-phase method, a phosphor layer deposited on a support inevitably has a distribution of phosphor thickness. This makes it difficult to obtain a uniform contact between the phosphor layer and a planar light-receiving element. In the presence of gaps between the phosphor layer and the planar light-receiving element, static electricity is produced by factors such as vibrations to increase the probability that image unevenness called microphonic noises occurs.

The present invention has been made in order to solve the problems discussed above. It is therefore an object of the invention to provide a scintillator panel realizing reduced image unevenness and small in-plane distribution of MTF (modulation transfer function) by virtue of having a cushioning layer between a support and a phosphor. The cushioning layer absorbs irregularities on the phosphor layer when the scintillator panel is compression bonded to a planar light-receiving element (a sensor panel) by the application of a pressure to the phosphor layer from the support side, and thereby allows the phosphor layer to be in uniform contact with the planar light-receiving element without any gaps in the interface.

Solution to Problem

The present invention has the following configurations.

A scintillator panel according to the present invention includes, in the order named, a support, a cushioning layer disposed on a surface of the support, and a phosphor layer deposited on the surface of the cushioning layer, the cushioning layer having a thickness larger than the difference between the largest value and the smallest value of the thickness of the phosphor layer, the phosphor layer being configured to be placed into uniform contact with a surface of a planar light-receiving element when the phosphor layer is pressed against the planar light-receiving element by the application of a pressure from the support side through the cushioning layer.

The cushioning layer preferably includes light-reflecting particles or light-absorbing particles.

The light-reflecting particles preferably include at least titanium dioxide.

The scintillator panel preferably has electric conductivity.

The support is preferably based on a resin.

A method for producing a scintillator panel according to the present invention includes forming a cushioning layer on a surface of a support and forming a phosphor layer on the surface of the cushioning layer by a deposition method, the cushioning layer being formed on the support so as to have a thickness enough to surpass a difference expected between the largest value and the smallest value of the thickness of the phosphor layer, the phosphor layer being formed on the cushioning layer so that the phosphor layer is allowed to be placed into uniform contact with a surface of a planar light-receiving element when the phosphor layer is pressed against the planar light-receiving element by the application of a pressure from the support side through the cushioning layer.

The cushioning layer preferably includes light-reflecting particles or light-absorbing particles.

The light-reflecting particles preferably include at least titanium dioxide.

The scintillator panel preferably has electric conductivity.

The support is preferably based on a resin.

Advantageous Effects of Invention

According to the present invention, a cushioning layer is disposed between a support and a phosphor. When the scintillator panel is compression bonded to a planar light-receiving element (a sensor panel) by the application of a pressure to the phosphor layer from the support side, the cushioning layer absorbs irregularities on the phosphor layer and thereby eliminates any gaps in the interface between the planar light-receiving element and the phosphor layer. Thus, the image unevenness and the in-plane distribution of MTF are reduced.

BRIEF DESCRIPTION OF DRAWINGS

FIG. 1 is a schematic sectional view illustrating a configuration of a scintillator panel 10 as an example of scintillator panels.

FIG. 2 is an enlarged sectional view of the scintillator panel 10.

FIG. 3 is a schematic view illustrating a configuration of a deposition apparatus 81 as an example of deposition apparatuses.

FIG. 4 is a partially cutaway perspective view schematically illustrating a configuration of a radiographic image detector 100 as an example of radiographic image detectors.

FIG. 5 is an enlarged sectional view of an imaging panel 51 as an example of imaging panels.

FIG. 6 is a sectional view illustrating an example of deposition substrates of the invention, wherein there are shown materials and a middle line (JIS B 0601-2001) at half the height of surface roughness on a scintillator formation scheduled surface of a cushioning layer (the surface of the cushioning layer opposite to the surface in contact with a support).

FIG. 7 is a schematic view illustrating a typical example of the methods for producing deposition substrates of the invention.

FIG. 8 is a schematic view illustrating a typical example of the methods for forming a polyparaxylene protective layer on the surface of a phosphor layer of a scintillator panel.

FIG. 9 is a schematic view of a scintillator panel of the invention being placed into contact with a planar light-receiving element by the application of a pressure from the support side with the consequent deformation of a phosphor layer associated with the absorption of the thickness distribution of the phosphor layer into a cushioning layer.

DESCRIPTION OF EMBODIMENTS

Embodiments of the present invention will be described in detail hereinbelow with reference to the drawings.

The term "phosphors" or "scintillators" in the invention refers to fluorescent materials that absorb the energy of incident radiations such as X-rays and emit electromagnetic waves having wavelengths of 300 to 800 nm, namely, ultraviolet to infrared electromagnetic waves mainly in the visible light region.

[Scintillator Panels]
[Supports]

As illustrated in FIG. 1, a scintillator panel 10 includes a support 1. Examples of the materials of the supports include various glasses, ceramic materials, semiconductor materials, polymer materials, carbon materials and metals which are transmissive to radiations such as X-rays. Specific examples include glass plates such as quartz glass, borosilicate glass and chemically reinforced glass; ceramics such as sapphire, silicon nitride and silicon carbide; semiconductors such as silicon, germanium, gallium arsenide, gallium phosphide and gallium nitride; polymer materials such as cellulose esters (for example, cellulose acetate), polyethylene terephthalate, polyethylene naphthalate, polyamide, polyimide, acetate fibers, polycarbonate and bionanofibers; carbon materials such as amorphous carbon and carbon fiber-reinforced plastics (CFRP); and metals such as aluminum, iron and copper, and metal materials having layers of oxides of these metals.

These materials may be used singly or in the form of a stack.

Of the above materials of the supports 1, those polymer materials having an elastic modulus of 0.1 to 20 GPa are particularly preferable. With this elastic modulus, the support 1 can hold a phosphor layer 2 and can also serve as an auxiliary cushioning layer. Here, the term "elastic modulus" indicates a value obtained by testing a JIS-C2318 sample with a tensile tester and calculating the ratio of the stress over the strain indicated by the gauge marks on the sample in the range in which the strain stress curve shows a straight relationship. This ratio is called the Young's modulus. In the specification, this Young's modulus is defined as the elastic modulus.

Specific examples include polyethylene naphthalate (6 to 8 GPa, for example, 7 GPa), polyethylene terephthalate (3 to 5 GPa, for example, 4 GPa), polycarbonate (1 to 3 GPa, for example, 2 GPa), polyimide (6 to 8 GPa, for example, 7 GPa), polyetherimide (2 to 4 GPa, for example, 3 GPa), aramid (11 to 13 GPa, for example, 12 GPa), polysulfone (1 to 3 GPa, for example, 2 GPa) and polyether sulfone (1 to 3 GPa, for example, 2 GPa) (elastic moduli in parentheses). The values of elastic modulus are variable even among polymer films of the same material, and the values in parentheses are not absolutely correct and should be considered as guides. The above polymer materials are preferable also because of their high heat resistance and durability in the deposition of phosphors. In particular, polyimide has particularly high heat resistance and is suitable for use in the case where columnar crystals of a phosphor (a scintillator) are formed on a cushioning layer 3 by a gas-phase method using cesium iodide (CsI) as the raw material.

The use of a bionanofiber film as the support 1 provides benefits in terms of the characteristics and environmental friendliness of the support 1 because the bionanofibers have characteristics which are not possessed by existing glasses or plastics such as (i) low weight, (ii) strength five times or more greater than iron (high strength), (iii) resistance to swelling by heat (low thermal expansion properties), (iv) being flexible (excellent flexibility), (v) processability by various treatments such as mixing, coating and film production, and (vi) combustibility of plant fiber materials.

In order to, for example, adjust the reflectance of the support 1, light-absorbing properties, light-reflecting properties or light-shielding properties may be imparted to the support, or the support may be colored.

Examples of the supports 1 having light-absorbing properties include colored polymer materials such as polyimide, polyetherimide and aramid, polymer materials containing coloring materials such as pigments described later, and colored ceramics such as amorphous carbon. Examples of the supports 1 having light-reflecting properties include metal materials such as aluminum, and polymer materials in which reflective particles such as white PET are dispersed. Examples of the supports 1 having light-shielding properties include various metal materials.

Examples of the pigments which may be added to impart light-absorbing properties include insoluble azo pigments such as First Yellow, Disazo Yellow, Pyrazolone Orange, Lake Red 4R and Naphthol Red; condensed azo pigments such as Cromophtal Yellow and Cromophtal Red; azo lake pigments such as Lithol Red, Lake Red C, Watching Red, Brilliant Carmine 6B and Bordeaux 10B; nitroso pigments such as Naphthol Green B; nitro pigments such as Naphthol Yellow S; phthalocyanine pigments such as Phthalocyanine Blue, First Sky Blue and Phthalocyanine Green; threne pigments such as Anthrapyrimidine Yellow, Perinone Orange, Perylene Red, Thioindigo Red and Indanthrone Blue; quinacridone pigments such as Quinacridone Red and Quinacridone Violet; dioxadine pigments such as Dioxadine Violet; isoindolinone pigments such as Isoindolinone Yellow; acidic dye lakes such as Peacock Blue Lake and Alkali Blue Lake; and basic dye lakes such as Rhodamine Lake, Methyl Violet Lake and Malachite Green Lake.

The pigments are preferably used in amounts of 0.01 to 10 parts by weight with respect to 100 parts by weight of the material of the support 1. This amount of the pigments ensures sufficient coloring of the films and prevents deteriorations in mechanical properties such as elongation and strength of the material of the support 1 due to excessive addition of the pigments over the saturated coloration.

[Cushioning Layers]

The scintillator panel 10 includes a cushioning layer 3 that is based on an elastic resin and is disposed on the support 1. When the scintillator panel 10 is compression bonded to a planar light-receiving element (a sensor panel) by the application of a pressure to a phosphor layer 2 from the support 1 side, projections on the surface of the phosphor layer 2 are pressed down into the cushioning layer 3 and the phosphor layer 2 is allowed to be placed into uniform contact with the planar light-receiving element. In this manner, the cushioning layer 3 disposed between the support 1 and the phosphor layer 2 serves to prevent the generation of static electricity by vibrations.

The materials of the cushioning layers 3 are preferably soft resins capable of absorbing irregularities on the phosphor layers 2. Specific examples include vinyl chloride copolymers such as vinyl chloride-vinyl acetate copolymers, vinyl chloride-vinylidene chloride copolymers and vinyl chloride-acrylonitrile copolymers; synthetic rubbers and other resins such as silicone resins, acrylic resins, polyurethane resins, polyamide resins, butyral resins (for example, polyvinylbutyral), polyester resins, cellulose derivatives (for example, nitrocellulose), polyparaxylylenes, butadiene-acrylonitrile copolymers and styrene-butadiene copolymers; and thermosetting resins such as phenolic resins, epoxy resins (for example, phenoxy resins), urea resins, melamine resins and urea formamide resins. Of these, hydrophobic resins such as polyester resins, polyurethane resins and butyral resins are preferable in view of the fact that CsI (cesium iodide) is deliquescent. Two or more of the above resins may be used in combination. In particular, film properties may be advantageously controlled easily by using two or more kinds of resins having a difference in glass transition temperature (Tg) of 5° C. or more. The resins used in this case may belong to the same or different categories as long as their glass transition temperatures are different.

The cushioning layer 3 preferably has an elastic modulus of 0.001 to 10 GPa, more preferably 0.01 to 5 GPa, and still more preferably 0.01 to 1 GPa. When the elastic modulus of the cushioning layer 3 is 0.001 GPa or more, the cushioning layer 3 exhibits low surface tackiness and will not collect foreign matters during production. Consequently, the occurrence of image defects tends to be reduced. When, on the other hand, the elastic modulus of the cushioning layer 3 is 10 GPa or less, the cushioning layer 3 can absorb projections on the surface of the phosphor layer 2 and allows the phosphor layer 2 to be placed into uniform contact with a planar light-receiving element, making it easy to prevent the generation of static electricity by vibrations.

The thickness of the cushioning layer 3 needs to be larger than the difference between the largest value and the smallest value of the thickness of the phosphor layer 2. The thickness of the cushioning layer 3 is preferably 1.5 to 30 times, more preferably 2 to 10 times, and still more preferably 2 to 5 times greater than the difference between the largest value and the smallest value of the thickness of the phosphor layer 2. Specifically, the thickness of the cushioning layer 3 is usually in the range of 10 to 300 μm, and preferably 30 to 100 μm. When the thickness of the cushioning layer 3 is 1.5 times or more the difference, the cushioning layer 3 can easily absorb projections on the surface of the phosphor layer 2 and allows the phosphor layer 2 to be placed into uniform contact with a planar light-receiving element, thus easily preventing the generation of static electricity by vibrations. On the other hand, limiting the thickness of the cushioning layer 3 to 30 times or less the difference tends to ensure that the residual stress after the film production will not cause large warpage of the support 1. Such a support 1 allows the phosphor layer 2 to be deposited thereon while ensuring that the phosphor layer 2 will not be cracked and good image quality (in particular, sharpness) tends to be obtained.

The cushioning layer 3 may be a single layer or may include two or more layers.

In the invention, the scintillator panel 10 is compression bonded to a planar light-receiving element by the application of a pressure to the phosphor layer 2 from the support 1 side. The method for pressing the phosphor layer 2 is not particularly limited. Examples of such methods include pressing with elastic bodies such as cushions, atmospheric pressing by vacuum sealing, and mechanical pressing with tools such as screws.

The cushioning layer 3 may contain a filler. Examples of the fillers include light-reflecting particles and light-absorbing particles that give light-reflecting or light-absorbing properties to the cushioning layer 3.

The light-reflecting particles added to the cushioning layer 3 have a function to enhance sharpness by preventing the light generated in the phosphor layer 2 from being optically diffused in the cushioning layer 3, and also have a function to enhance sensitivity by effectively directing the light that has reached the cushioning layer 3 back to the columnar crystals of the phosphor layer 2.

The light-reflecting particles may be commercial products described later or may be produced by known methods.

The light-reflecting particles are not particularly limited and may be any of particulate materials having a different refractive index from the material forming the cushioning layer 3. Examples of such materials include alumina, yttrium oxide, zirconium oxide, titanium dioxide, barium sulfate, silica, zinc oxide, calcium carbonate, glasses and resins. These may be used singly, or two or more may be used as a mixture. (The mixture may include two or more materials belonging to different categories such as glass and resin, may include two or more materials belonging to the same category such as acrylic resin and polyester resin in the resin category, or may include one or more materials belonging to one category and two or more materials belonging to another category such as glass, acrylic resin and polyester resin.)

Of such materials, for example, glass beads and resin beads, in particular, glass beads are preferable because the refractive index may be adjusted freely and optical diffusion properties may be controlled easily as compared to metal oxides.

Glass beads having a higher refractive index are more preferable. Examples thereof include BK7 (n (relative refractive index, the same applies hereinafter)=about 1.5); LaSFN9 (n=about 1.9); SF11 (n=about 1.8); F2 (n=about 1.6); BaK1 (n=about 1.6); barium titanate (n=about 1.9); high refractive index blue glass (n=about 1.6 to 1.7); $TiO_2$—BaO (n=about 1.9 to 2.2); borosilicate (n=about 1.6); and chalcogenide glass (n=about 2 or more). Examples of the resin beads include acrylic particles, polyester resin particles, polyolefin particles and silicone particles, with specific suitable examples including CHEMISNOW® (manufactured by Soken Chemical & Engineering Co., Ltd.), Silicone Resins KR Series (manufactured by Shin-Etsu Chemical Co., Ltd.), and TECHPOLYMER® (manufactured by SEKISUI PLASTICS CO., LTD.).

White pigments such as titanium dioxide have high opacifying properties and a high refractive index, and can easily scatter the light emitted from the scintillator by reflecting and refracting the light. Thus, the use of such pigments allows for marked improvements in the sensitivity of devices such as radiographic image conversion panels including the scintillator panel 10.

The light-reflecting particles are particularly preferably titanium dioxide in view of the facts that this material is easily available and has a high refractive index.

When titanium dioxide is used as the light-reflecting particles, the titanium dioxide may be one which has been surface treated with inorganic compounds or organic compounds in order to improve dispersibility and workability. For example, the surface-treated titanium dioxides and the surface treatment methods are disclosed in JP-A-S52-35625, JP-A-S55-10865, JP-A-S57-35855, JP-A-S62-25753, JP-A-S62-103635 and JP-A-H09-050093. For the surface treatment, inorganic compounds such as aluminum oxide hydrate, hydrous zinc oxide and silicon dioxide, and organic compounds such as dihydric to tetrahydric alcohols, trimethylolamine, titanate coupling agents and silane coupling agents may be preferably used as the surface-treatment agents. The amounts of the surface-treatment agents may be determined appropriately in accordance with purposes as described in the above patent literatures.

The crystal structure of the titanium dioxide may be any of rutile, brookite and anatase forms. However, the rutile form is particularly preferable because its refractive index has a high ratio to that of resins to realize high brightness as well as from points of view such as the reflectance with respect to visible light.

Examples of titanium dioxides include those produced by a hydrochloric acid process such as CR-50, CR-50-2, CR-57, CR-80, CR-90, CR-93, CR-95, CR-97, CR-60-2, CR-63, CR-67, CR-58, CR-58-2 and CR-85; and those produced by a sulfuric acid process such as R-820, R-830, R-930, R-550, R-630, R-680, R-670, R-580, R-780, R-780-2, R-850, R-855, A-100, A-220 and W-10 (product names, manufactured by ISHIHARA SANGYO KAISHA, LTD.).

From the viewpoint of reflectance, the area average particle diameter of the titanium dioxide is preferably 0.1 to 5.0 µm, and more preferably 0.2 to 0.3 µm. In order to improve the affinity and dispersibility for polymers as well as to suppress a degradation of polymers, the titanium dioxide is particularly preferably one which has been surface treated with oxides of metals such as Al, Si, Zr and Zn.

The use of titanium dioxide as the light-reflecting particles tends to cause a decrease in the reflectance to light with wavelengths of 400 nm or less and to cause a degradation of binders due to the photocatalytic action of titanium dioxide. In view of these facts, it is preferable to use the titanium dioxide in combination with at least one kind of light-reflecting particles selected from barium sulfate, alumina, yttrium oxide and zirconium oxide which have a high reflectance even to 400 nm and less wavelengths. In particular, barium sulfate is more preferable because its reflectance in the range of wavelengths of 400 nm and less is high. The mass ratio of barium sulfate to titanium dioxide is preferably 95:5 to 5:95, and more preferably 20:80 to 5:95.

Further, it is preferable that the light-reflecting particles include at least one selected from solid particles and void particles.

The void particles are not particularly limited as long as the particles have voids. Examples thereof include single-hollow particles having one hollow portion within the particle, multi-hollow particles having a number of hollow portions within the particle, and porous particles. These particles may be selected appropriately in accordance with the purpose.

Of the void particles, multi-hollow particles and porous particles are preferable.

Here, the term "void particles" refers to particles having voids such as hollow portions and pores.

The term "hollow portions" refers to holes (air layers) in the inside of the particles.

Due to the difference in refractive index between the holes (the air layers) and the shells (such as resin layers), the hollow particles can add optical reflection and diffusion characteristics to the cushioning layer 3 which cannot be obtained with solid particles.

The term "multi-hollow particles" refers to particles having a plurality of such holes in the inside of particles. The term "porous particles" refers to particles having pores in the particle. The term "pores" refers to portions that are inwardly curved or recessed from the surface toward the inside of the particle. Examples of the shapes of the pores include cavities, and needle-like shapes or curved shapes which are depressed toward the inside or the core of the particles. The pores may be present across the particles. The sizes and the volumes of the pores may be variable and are not particularly limited.

The materials of the void particles are not particularly limited and may be selected appropriately in accordance with the purpose. Examples thereof include the aforementioned materials. In particular, suitable examples include thermoplastic resins such as styrene/acryl copolymers.

The void particles may be appropriately produced or are available in the market. Examples of the commercially available products include ROPAQUE HP1055 and ROPAQUE HP433J (manufactured by ZEON CORPORATION), and SX866 (manufactured by JSR Corporation).

Suitable examples of these multi-hollow particles include Sylosphere® and Sylophobic® manufactured by FUJI SILYSIA CHEMICAL LTD.

Of the void particles, multi-hollow particles are particularly preferable in terms of void content.

The light-reflecting particles in the form of void particles may have a single kind of the above void configurations or may have two or more kinds of the void configurations. The void particles may be used in combination with solid particles.

The void particles may be advantageously used in combination with white pigments such as titanium dioxide, alumina, yttrium oxide, zirconium oxide and barium sulfate. This combined use prevents deteriorations in scintillator characteristics due to the white pigments adsorbing water ($H_2O$) and carbon dioxide ($CO_2$) to their surface and releasing them when exposed to heat or X-ray energy. That is, the combined use of the void particles and the white pigments suppresses the release of impurity gases such as water ($H_2O$) and carbon dioxide ($CO_2$) from the white pigments and thus prevents deteriorations in scintillator characteristics.

Alternatively, deteriorations of scintillators due to the detachment of water ($H_2O$) and carbon dioxide ($CO_2$) from the surface of white pigments may be effectively prevented by forming a large number of bubbles in the cushioning layer 3 including a white pigment and a binder resin described later. According to this method, the white pigment and the bubbles having a large difference in refractive index are placed in contact with each other in the cushioning layer 3. This configuration increases the difference in reflectance between the materials constituting the cushioning layer 3, resulting in an increase in the reflectance of the cushioning layer 3.

The area average particle diameter of the light-reflecting particles is preferably 0.1 µm to 5.0 µm from points of view such as the reflectance of the cushioning layer 3 and the stability of a coating liquid for forming the cushioning layer 3 while ensuring the prevention of surface cracks. (Hereinafter, the coating liquid will be also written as the "cushioning layer-forming liquid". The same applies to coating liquids for other purposes.) This area average particle diameter of the light-reflecting particles ensures that optical scattering in the cushioning layer 3 occurs efficiently to decrease the transparency and to increase the reflectance, as well as that the cushioning layer-forming liquid exhibits improved over-time stability and the occurrence of cracks in the cushioning layer 3 during drying after the application is avoided.

From the point of view of the dispersibility of the light-scattering particles in the cushioning layer, the grain size distribution of the light-reflecting particles is preferably in the range of 0.05 to 10.0 µm.

The light-reflecting particles usually represent 3 to 70 vol %, and preferably 10 to 50 vol % of the total volume of the components constituting the cushioning layer 3 taken as 100 vol %. The light-reflecting particles present in this volume percentage provide an enhancement in reflectance without deteriorating the function of the cushioning layer 3 and consequently the sensitivity of the scintillator panel 10 is enhanced. Further, improved adhesion tends to be obtained between the phosphor layer 2 and the cushioning layer 3 or between the support 1 and the cushioning layer 3.

Further, it is preferable that the cushioning layer 3 containing the light-reflecting particles contain voids in an amount of 5 to 30 vol %.

The light-absorbing particles added to the cushioning layer 3 serve purposes such as to facilitate the control of the reflectance of the support 1 cushioning layer to a desired value with high accuracy. Examples of the light-absorbing particles include light-absorbing pigments.

The light-absorbing pigments may be any of known various such pigments. Suitable pigments are those capable of absorbing long-wavelength red light components which are more prone to scatter, and blue coloring materials are preferable. Preferred examples of the blue coloring materials include ultramarine blue and Prussian blue (iron ferrocyanide). Further, organic blue pigments such as phthalocyanine, anthraquinone, indigoid and carbonium may also be used. Of these, phthalocyanine is preferable from points of view such as the radiation durability and the UV durability of light-absorbing pigment layers. Furthermore, titanium-containing black pigments such as titanium black may be suitably used. Titanium black is a black substance resulting from partial removal of oxygen from titanium dioxide. Because its specific gravity is the same as titanium dioxide, a cushioning layer-forming liquid including titanium dioxide as the light-scattering particles and titanium black exhibits high stability. The reflectance of deposition substrates may be advantageously adjusted easily by controlling the mixing ratio of titanium dioxide to titanium black. From the point of view of light-absorbing properties, the pigments are preferably present in amounts of 3 to 70 vol % relative to the total volume of the components constituting the cushioning layer 3 taken as 100 vol %.

In the specification, the term "deposition substrate" refers to the support on which the cushioning layer has been formed.

[Phosphor Layers]

As illustrated in FIG. 2, a phosphor layer 2 is comprised of columnar crystals 2a grown from the cushioning layer 3 so as to form an interface between the layers.

Examples of the materials for the phosphor layers 2 include known phosphors such as sodium fluoride (NaF), sodium chloride (NaCl), sodium bromide (NaBr), sodium iodide (NaI), potassium fluoride (KF), potassium chloride (KCl), potassium bromide (KBr), potassium iodide (KI), rubidium fluoride (RbF), rubidium chloride (RbCl), rubidium bromide (RbBr), rubidium iodide (RbI), cesium fluoride (CsF), cesium chloride (CsCl), cesium bromide (CsBr) and cesium iodide (CsI). Of these, CsI is preferable because the X-ray to visible light conversion ratio is relatively high, columnar crystals are formed easily by deposition, and the scattering of light in the crystals is suppressed by the light guide effects ascribed to the crystal structure and consequently the thickness of the phosphor layer 2 may be increased correspondingly.

Because the luminous efficiency obtained with CsI alone is low, the phosphor layer 2 preferably includes CsI in combination with any of various activators. Examples of such phosphor layers 2 include a phosphor layer 2 disclosed in JP-B-S54-35060 which contains CsI and sodium iodide (NaI) in an appropriate molar ratio. Another example is a phosphor layer 2 disclosed in JP-A-2001-59899 which contains CsI and activators such as thallium (Tl), europium (Eu), indium (In), lithium (Li), potassium (K), rubidium (Rb) and sodium (Na) in an appropriate molar ratio.

In the scintillator panel 10 of the invention, the phosphor layer 2 is particularly preferably a phosphor layer 2 obtained from cesium iodide and an activator(s) including one or more thallium compounds as the raw materials. In particular, thallium-activated cesium iodide (CsI:Tl) is preferable because this material has a wide range of emission wavelengths from 300 to 750 nm.

The thallium compound may be any of various thallium compounds (thallium (I) compounds and thallium (III) compounds). Examples include thallium iodide (TlI), thallium bromide (TlBr), thallium chloride (TlCl) and thallium fluoride (TlF and $TlF_3$). In particular, thallium iodide (TlI) is preferable because of its high degree of CsI activation.

The thallium compounds preferably have a melting point in the range of 400 to 700° C. This melting point of the thallium compounds ensures that the activator is uniformly distributed in the columnar crystals in the phosphor layer 2 formed by deposition, resulting in an improvement in luminous efficiency. Herein, the melting point is measured at normal pressure (usually about 0.101 MPa).

The relative content of the activators in the phosphor layer 2 of the invention is preferably 0.1 to 5 mol %.

In the specification, the relative content of the activators is the molar percentage of the activators relative to the phosphor matrix compound taken as 100 mol %. Here, the phosphor matrix compound refers to the phosphor itself such as CsI that is not activated with activators. The raw materials that form the phosphor layers 2 such as the phosphor matrix compounds and the activators are collectively referred to as the phosphor raw materials.

The phosphor layer 2 may be a single layer, or may include two or more layers.

Of the phosphor layers 2, a preferred phosphor layer 2 includes a phosphor main layer that includes a phosphor matrix compound and an activator, and a phosphor underlayer that is disposed between the support 1 and the phosphor main layer, includes a phosphor matrix compound alone or together with an activator, and has a lower void content than the phosphor main layer.

When the phosphor underlayer includes an activator, the relative content of the activator in the underlayer is preferably 0.01 to 1 mol %, and more preferably 0.1 to 0.7 mol %.

In particular, the relative content of the activator in the phosphor underlayer is highly preferably not less than 0.01 mol % in terms of the enhancement of emission brightness as well as the storage properties of the scintillator panel 10.

In the invention, it is highly preferable that the relative content of the activator in the phosphor underlayer be lower than the relative content of the activator in the phosphor main layer. The ratio of the relative content of the activator in the phosphor underlayer to the relative content of the activator in the phosphor main layer ((Relative content of activator in phosphor underlayer)/(Relative content of activator in phosphor main layer)) is preferably 0.1 to 0.7.

From viewpoints such as the luminous efficiency of the phosphor layer 2, the degree of orientation based on an X-ray diffraction spectrum with respect to a plane of the phosphor in the phosphor layer 2 having a certain plane index is preferably in the range of 80 to 100% at any position in the direction of layer thickness. For example, the plane index in the columnar crystals of thallium-activated cesium iodide (CsI:Tl) may be any of indices including (100), (110), (111), (200), (211), (220) and (311), and is preferably (200). (For the plane indices, refer to X-Sen Kaiseki Nyuumon (Introduction to X-ray analysis) (Tokyo Kagaku Dojin), pp. 42-46.)

Herein, the "degree of orientation based on an X-ray diffraction spectrum with respect to a plane having a certain plane index" indicates the proportion of the intensity Ix of the certain plane index relative to the total intensity I of the total including planes with other plane indices. For example, the degree of orientation of the intensity I200 of the (200) plane in an X-ray diffraction spectrum is obtained by: "Degree of orientation=I200/I".

For example, the plane indices for the determination of the orientation degree may be measured by X-ray diffractometry (XRD) (crystal X-ray diffractometry or powder X-ray diffractometry). The X-ray diffractometry is a versatile analytical technique capable of identifying substances or giving information about structures such as crystal phase structures by utilizing a phenomenon in which a characteristic X-ray having a specific wavelength is diffracted by crystalline substances according to the Bragg's equation. The illumination targets may be Cu, Fe and Co, and the illumination outputs are generally about 0 to 50 mA and about 0 to 50 kV in accordance with the performance of the apparatus.

The thickness of the phosphor layer 2 is preferably 100 to 800 μm, and more preferably 120 to 700 μm because a good balance is obtained between the brightness of the scintillator panel 10 and the sharpness of the obtainable radiographic images.

[Additional Layers]

The scintillator panel 10 of the invention may have an additional layer such as a reflective layer, an adhesive layer or a conductive layer between, for example, the support 1 and the cushioning layer 3. The scintillator panel may have a conductive layer on the backside of the support 1 (on the surface opposite to the phosphor layer 2).

The addition of a reflective layer makes it possible to extract the phosphor light with very high efficiency, resulting in an enhancement in sensitivity. The reflective layer may be formed of the light-reflecting particles described as the filler for optional use in the cushioning layer 3, and a specific binder resin, or may be a metal layer.

Preferred examples of the metal materials for forming the reflective layers include aluminum, silver, platinum, palladium, gold, copper, iron, nickel, chromium, cobalt, stainless steel and neodymium. From the point of view of reflectance, those metal materials based on aluminum or silver are most preferable. When silver is used for the reflective layer, a dissimilar metal may be added in order to increase the corrosion resistance. The metals that are added are not particularly limited. Preferred examples thereof include gold, palladium, copper and neodymium.

Such metals may be applied to cover the polymer sheets by any methods without limitation such as deposition, sputtering and metal foil lamination. From the point of view of the adhesion to the polymer sheets, sputtering is most preferable.

The reflective layer may be a single layer, or may include two or more layers.

The adhesive layer may be formed using any of the materials described as the resins for use in the cushioning layer 3. From the point of view of the adhesion with respect to a planar light-receiving element, the thickness of the adhesive layer is usually 0.1 to 100 μm, preferably 1 to 20 μm, and more preferably 3 to 10 μm.

The conductive layers are made of such materials as metals, conductive polymers, conductive oxides and carbon materials. Specifically, the layers include metals such as aluminum, copper and iron, conductive polymers such as polythiophene, polypyrrole and polyaniline, and oxides such as tin-doped indium oxide, antimony-doped tin oxide and zinc oxide. The addition of the conductive layer makes it possible to further suppress the generation of static electricity which may cause unevenness in images.

The conductivity of the conductive layer is usually not more than $1.0 \times 10^{12} \Omega/\square$, and preferably not more than $1.0 \times 10^{12} \Omega/\square$.

The support 1 may also serve as a conductive layer. For example, carbon materials such as amorphous carbon and carbon fiber-reinforced plastics (CFRP) and metal materials such as aluminum, iron and copper may be used as the supports also serving as conductive layers.

[Protective Layers]

Where necessary, the scintillator panel 10 of the invention may have a protective layer which physically or chemically protects the phosphor layer 2. From points of view such as the prevention of the deliquescence of the phosphor in the phosphor layer 2, it is preferable that the entire surface of the phosphor layer 2 opposite to the support 1 be covered with a continuous protective layer, and it is more preferable that the entire surface of the phosphor layer 2 and a portion of the cushioning layer 3 of the scintillator panel 10 be covered with a continuous protective layer.

Here, the "entire surface of the phosphor layer" refers to all the regions of the columnar phosphor crystal layer including the surface opposite to the surface in contact with the deposition substrate as well as the lateral sides (in other words, all the surfaces which are not in contact with the deposition substrate). Further, the "portion of the cushioning layer" refers to all the regions of the cushioning layer 3 which are not in contact with the phosphor layer 2 or the support 1 and are exposed to the atmosphere (in other words, the lateral sides of the cushioning layer). The term "continuous protective layer" means that the protective layer covers the regions to be protected without any bare spots.

The protective layer may be formed of a single material, a mixed material, or a plurality of films or the like including different materials.

As mentioned above, the main purpose of the protective layer in the invention is to protect the phosphor layer 2. In detail, cesium iodide (CsI) as an example of the phosphors is highly hygroscopic and deliquesces when left in the air by absorbing vapor in the air. To prevent this, the protective layer is disposed in the scintillator panel 10.

The protective layer also serves to block substances (such as halogen ions) released from the phosphor in the scintillator panel 10 and to prevent the corrosion of a planar light-receiving element placed in contact with the phosphor layer.

In a configuration in which the phosphor layer 2 formed of columnar phosphor crystals in the scintillator panel 10 and a planar light-receiving element are coupled together through a medium such as an adhesive or an optical oil, the protective layer also serves as an anti-penetration layer preventing the penetration of the adhesive or the optical oil into the spaces between the columnar phosphor crystals.

Preferred materials for forming the protective layer include polyolefin resins, polyacetal resins, epoxy resins, polyimide resins, silicone resins and polyparaxylylene resins. The polyparaxylylene resins may be applied by a CVD method, and the other materials may be applied by a coating method. Examples of the polyparaxylylene resins include polyparaxylylene, polymonochloroparaxylylene, polydichloroparaxylylene, polytetrachloroparaxylylene, polyfluoroparaxylylene, polytetrachloroparaxylylene, polydimethylparaxylylene and polydiethylparaxylylene.

From the viewpoints of appropriate protection of the phosphor layer 2 as well as the strength and the flexibility of the scintillator panel 10, the thickness of the protective layer is preferably 0.1 to 2000 μm.

In the case where the protective layer is a film including a polyparaxylylene resin, the film thickness is preferably 2 to 15 μm from the viewpoints of the sharpness of radiographic images and the moisture proofness of the protective layer. In the case where the protective layer is bonded to a planar light-receiving element, the thickness of the adhesive layer is preferably not less than 10 μm in order to ensure adhesion, and the total thickness of the protective layer and the adhesive layer is preferably not more than 20 μm. When the total thickness of the polyparaxylylene layer and the adhesive layer is not more than 20 μm, the protective layer and a planar light-receiving element may be bonded while the scattering of light in the gap between the planar light-receiving element and the scintillator panel 10 is suppressed and thus a decrease in sharpness can be advantageously prevented.

The protective layer that includes a polymer material other than the polyparaxylene resins may be formed also by applying a polymer film including the polymer material (a protective film) onto the phosphor layer 2 (on part or all of the surfaces which are not in contact with layers such as the reflective layer and are exposed to the atmosphere).

In another embodiment, a hot melt resin layer may be formed on the phosphor layer 2 so as to serve as a protective layer. In this case, the hot melt resin also functions to bond the surface of the phosphor layer of the scintillator panel 10 to the surface of a planar light-receiving element, in addition to the protective function.

Herein, the term "hot melt resin" refers to an adhesive resin which is free from water or solvents and is solid at room temperature (usually about 25° C.) and which includes a nonvolatile thermoplastic material. The hot melt resins become molten when the resin temperature is above the melting onset temperature by heating or the like, and become solid when the resin temperature falls to or below the solidification temperature. Further, the hot melt resins exhibit tackiness in the thermally molten state and become non-tacky in the solid state when the resin temperature is decreased to or below the solidification temperature (for example, to normal temperature).

Suitable hot melt resins are those based on polyolefin resins, polyester resins or polyamide resins, but are not limited thereto. Of these, polyolefin resins are more preferable in view of light transmission properties.

From viewpoints such as continuous use characteristics and the prevention of adhesive separation in planar light-receiving elements such as thin film transistors (TFTs), the melting onset temperature of the hot melt resins is preferably 60 to 150° C. The melting onset temperature of the hot melt resins may be adjusted by the addition of plasticizers.

The thickness of the hot melt resin is preferably not more than 30 μm.

Of the configurations described above, it is preferable to cover the entirety of the top and lateral sides of the phosphor layer 2 as well as the periphery of the deposition substrate around the phosphor layer with polyparaxylene. According to this configuration, high moisture proofness is obtained.

The haze of the protective layer is preferably 3 to 40%, and more preferably 3 to 10% in consideration of properties such as the sharpness of the obtainable radiographic images, the unevenness of radiographic images, and the production stability and the workability in the production of scintillator panels. For example, materials having a haze in the above range may be appropriately selected from commercial polymer films and readily purchased from the market, or may be produced in accordance with the processes for the manufacturing of such polymer films. The haze is a value measured with NDH5000W manufactured by NIPPON DENSHOKU INDUSTRIES CO., LTD.

The optical transmittance of the protective layer is preferably not less than 70% with respect to 550 nm light in consideration of properties such as the photoelectric conversion efficiency of the scintillator panel 10 and the wavelengths of the phosphor light. It is, however, practically preferable that the optical transmittance be 99% to 70% because materials (such as films) having an optical transmittance of 99% or above are difficult to obtain in industry.

The moisture permeability of the protective layer measured at 40° C. and 90% RH in accordance with JIS Z0208 is preferably not more than 50 $g/m^2 \cdot day$, and more preferably not more than 10 $g/m^2 \cdot day$ from points of view such as the protection and the deliquescence of the phosphor layer 2. It is, however, practically preferable that the moisture permeability be 0.01 to 50 $g/m^2 \cdot day$, and more preferably 0.1 to 10 $g/m^2 \cdot day$ because films having a moisture permeability of 0.01 $g/m^2 \cdot day$ or below are difficult to obtain in industry.

[Scintillator Panel Production Methods]

Methods for producing the scintillator panels 10 according to the present invention will be described. In the method for producing the scintillator panel 10, the phosphor layer 2 is deposited onto the surface of the cushioning layer 3 disposed on one surface of the support 1. As illustrated. In FIG. 9, the phosphor layer 2 is arranged to be opposed to a planar light-receiving element 20b and is pressed thereto by the application of a pressure from the support 1 side through the cushioning layer 3. Consequently, the phosphor layer 2 is deformed toward the cushioning layer 3 until the surface of the phosphor layer 2 is brought into close contact with the planar light-receiving element.

A typical example of the methods for producing the scintillator panels 10 will be described with reference to the drawings.

[Method for Forming Cushioning Layers]
〈Cushioning Layer Formation Procedures〉

The cushioning layers according to the invention may be formed (the deposition substrates may be produced) by adopting an appropriate known method in accordance with the purpose. Here, a typical example will be described with reference to FIG. 7.

FIG. 7 is a schematic view illustrating a typical example of the methods for forming the cushioning layers of the invention.

In the typical example of the methods for forming the cushioning layers of the invention, a deposition substrate production apparatus 109 schematically illustrated in FIG. 7 is used. The deposition substrate production method involving the production apparatus 109 preferably includes a workpiece (support) feed step 29, an application step 39, drying steps 49 and 89, a heat treatment step 59, and a recovery step 69.

In the feed step 29, a feeder (not shown) is used.

In the feed step 29, a roll support 202 wound by the feeder around a core is dispensed by the feeder and the support is fed to the subsequent application step 39.

In the application step 39, an applicator 304 is used which includes a backup roll 301, an application head 302, and a vacuum chamber 303 disposed upstream from the application head 302.

In the application step 39, the support 1' continuously fed by the feeder in the feed step 29 is held by the backup roll 301, and the application head 302 applies a cushioning layer-forming liquid including components such as light-scattering particles, a binder resin, additives and a solvent. The cushioning layer-forming liquid is applied to the support 1' in such a manner that the vacuum chamber 303 disposed upstream from the application head 302 generates a vacuum to stabilize the bead (a pool of the coating liquid)

formed during the application between the support 1' and the cushioning layer-forming liquid supplied from the application head 302.

The vacuum chamber 303 is configured such that the degree of vacuum can be adjusted. The vacuum chamber 303 is connected to a vacuum blower (not shown), which evacuates the inside of the vacuum chamber. The vacuum chamber 303 is airtight, is located adjacent to the backup roll 301 with a small gap, and is evacuated to an appropriate degree of vacuum to suction the upstream of the bead (on the feeder side relative to the application head), thus allowing the coating liquid to form a stable bead.

The flow rate of the coating liquid ejected from the application head 302 is adjusted as required via a pump (not shown).

Although extrusion coating is illustrated above as an example of the application methods, any of other known application methods may also be used to apply the coating liquid, with examples including gravure coating, roll coating, spin coating, reverse coating, bar coating, screen coating, blade coating, air knife coating and dipping.

In the drying step 49, a dryer 401 is used.

In the drying step 49, the cushioning layer precursor formed by the application of the cushioning layer-forming liquid onto the support 1' in the application step 39 is dried by the dryer 401. The drying step 49 is usually performed so that the surface temperature of the cushioning layer precursor is raised to 80 to 200° C. In the drying step 49, the cushioning layer precursor is dried with a drying gas. The drying gas is introduced through a drying gas inlet 402 and is discharged through an outlet 403. The dryer is configured so that the temperature and the flow rate of the drying air including the drying gas can be set appropriately.

The drying step 89 has the same configuration as in the drying step 49, and thus detailed description thereof will be omitted. The drying step 89, in combination with the drying step 49, allows for the adjustment of the speed of drying of the cushioning layer precursor.

In the heat treatment step 59, the support 1' having the cushioning layer precursor is heat treated with a heat treatment apparatus 501 to remove volatile components in the cushioning layer precursor. The heat treatment is usually performed so that the surface temperature of the cushioning layer precursor reaches 150 to 250° C. In the heat treatment step, the cushioning layer precursor is heat treated with a heat treatment gas. The heat treatment gas is introduced through a heat treatment gas inlet 502 and is discharged through an outlet 503. The heat treatment apparatus is configured so that the temperature and the flow rate of the heat treatment gas including the drying gas heat treatment gas can be set appropriately.

Although not illustrated in the schematic view in FIG. 7, the heat treatment step 59 may be followed by a cooling step in which the support 1' having the cushioning layer (the deposition substrate) is cooled.

In the recovery step 69, the support 1' on which the cushioning layer film has been formed is wound with a winding machine (not shown). The reference sign 601 in FIG. 7 indicates a recovered roll of the support wound on a core.

Throughout the above steps, the support 1' having the coating film is conveyed on conveyor rolls a to d.

In the case where the cushioning layer is produced in a multilayer structure or an additional layer other than the cushioning layer is formed by application, the support on which the cushioning layer has been formed may be wound into a roll in the recovery step 69, and the wound support 601 may be set again as the support 1' in the feed step 29 and may be subjected to the same steps in which the cushioning layer-forming liquid or liquid for forming an additional layer other than the cushioning layer is applied onto the cushioning layer, dried and heat treated to form a stack including two or more cushioning layers or a stack including a cushioning layer and an additional layer other than the cushioning layer. Where necessary, the deposition substrate thus obtained may be heat treated to fusion bond the two or more cushioning layers into one layer.

In the method for forming the cushioning layer 3 of the invention, the surface temperature of the cushioning layer precursor is raised to 80 to 200° C. in the drying steps 49 and 89, and is increased to 150 to 250° C. in the heat treatment step 59. In this manner, the amount of volatile components (hereinafter, also written as the "volatile content") in the deposition substrate may be reduced to less than 5%. One of the characteristics of the deposition substrate production methods of the invention is that the heat treatment step is carried out after the drying steps to remove volatile components.

The surface temperature of the cushioning layer precursor formed on the support 1' may be measured with a known non-contact thermometer such as a laser thermometer or an infrared thermometer.

The temperature and the flow rate of the gases in the drying steps 49 and 89 and in the heat treatment step 59 are not particularly limited and may be appropriately adjusted based on the results of measurement with a non-contact thermometer such that the surface temperature of the coating film will fall in the above prescribed temperature range.

In the drying steps 49 and 89, it is preferable that the gas flow in a direction parallel to the plane of the support at a speed of 1 to 3 m/sec relative to the support 1' as measured at 5 mm above the surface of the coating film on the support 1'. When the speed of the gas relative to the support 1' at 5 mm above the coating film surface is in the above range, the cushioning layer can be dried without suffering problems such as roughening on the dried surface.

In the heat treatment step 59, the surface of the coating film may be heated with the heat treatment gas in combination with an infrared heater. Such a combined heat treatment advantageously increases the effects of the heat treatment on the cushioning layer on the support.

By the cushioning layer formation method of the invention described above, deposition substrates with less residual solvents and less adsorption of gas to the light-scattering particles may be obtained.

⟨Materials Used in Cushioning Layer Formation Method⟩

Hereinbelow, the support and the cushioning layer-forming liquid used in the cushioning layer formation method of the invention will be described.

<Supports 1'>

The materials of the supports 1' are as described hereinabove. In particular, polymer films are preferable from viewpoints such as that the production apparatus 109 illustrated in FIG. 7 may be suitably used, that the polymer films can be easily processed from roll to roll, and that the flexibility of the polymer films allows the scintillator panels to be intimately coupled to planar light-receiving elements. In order to prevent the deformation of the supports by heat applied during the deposition of phosphors onto the polymer films, the glass transition temperature of the polymer films is preferably not less than 100° C. In detail, suitable such polymer films are polyimide films.

Where necessary, additional layers such as the aforementioned light-shielding layers and light-absorbing layers may be appropriately disposed on the support. Further, the support itself may have light-shielding properties or reflecting properties.

The light-shielding layer may be provided on the support by any methods without limitation such as deposition, sputtering and metal foil lamination. From the viewpoint of the adhesion of the light-shielding layer with the support, sputtering is most preferable.

The light-absorbing pigment layer may be formed on the support by a method such as applying a coating liquid including the light-absorbing pigment onto the support followed by drying.

⟨Cushioning Layer-Forming Liquid⟩

The cushioning layer-forming liquid is prepared by dispersing or dissolving in a solvent individual components or a mixture of the components including light-scattering particles such as light-reflecting particles or light-absorbing particles, a binder resin as the matrix of the cushioning layer, and optional additives such as coloring materials including pigments, UV absorbers, fluorescent whitening agents, antistatic agents and dispersants. The procedures such as the sequence of the mixing of the components are not particularly limited as long as the object of the invention is not impaired.

The light-scattering particles, the binder resin and the additives may be dispersed or dissolved by any known dispersion or dissolution methods. Exemplary dispersing machines which may be suitably used include sand mills, Attritor, Pearl Mill, Super Mill, ball mills, impellers, dispersers, KD mills, colloid mills, Dynatron mills, three roll mills and pressure kneaders.

The details of the light-scattering particles, the binder resins, the coloring materials such as pigments, the UV absorbers and the fluorescent whitening agents are as described hereinabove.

The dispersants are added in order to help the light-scattering particles be dispersed in the binder resin. Various dispersants may be used in accordance with the binder resin and the light-scattering particles used. Examples thereof include polyhydric alcohols, amines, silicones, phthalic acid, stearic acid, caproic acid and lipophilic surfactants. The dispersants may remain in or may be removed from the cushioning layer that has been formed.

The dispersants are usually used in amounts of 0.05 to 10 parts by weight, and preferably 1 to 5 parts by weight with respect to 100 parts by weight of the binder resin.

The components such as the light-scattering particles, the binder resin and the additives may be dispersed or dissolved in any solvents without limitation. Examples of the solvents include lower alcohols (preferably alcohols having 1 to 6 carbon atoms) such as methanol, ethanol, n-propanol and n-butanol; chlorinated hydrocarbons such as methylene chloride and ethylene chloride; ketones such as acetone, methyl ethyl ketone (MEK), methyl isobutyl ketone and cyclohexanone; aromatic compounds such as toluene, benzene and xylene; ethers of lower fatty acids with lower alcohols such as methyl acetate, ethyl acetate and butyl acetate; esters such as dioxane, ethylene glycol monoethyl ether and ethylene glycol monomethyl ether; cyclohexane; and mixtures of these solvents.

The components such as the light-scattering particles, the binder resin and the additives may exhibit insufficient dispersibility in a single solvent. Further, the use of a single solvent may cause difficulties in controlling the solvent evaporation rate in the drying steps and tends to result in the roughening of the surface of the cushioning layer. To prevent such problems, it is preferable to use a mixed solvent including a plurality of compatible solvents having different amounts of evaporation heat. In particular, a mixed solvent including toluene, methyl ethyl ketone (MEK) and cyclohexanone is preferable.

When voids are to be introduced in the cushioning layer in the deposition substrate of the invention, the method for forming such voids is not particularly limited and may be selected appropriately in accordance with the purpose. Examples of the methods include (I) void particles are added to the cushioning layer, and (II) a cushioning layer-forming liquid containing bubbles or a foaming agent is applied onto the support to form a cushioning layer having a porous structure. In particular, the method (I) of adding void particles is preferable from the point of view of the easiness in the formation of the coating film. From the point of view of the void volume, the method (II) utilizing bubbles is preferable.

In the method (II) utilizing bubbles, the foaming agents may be appropriately selected from known foaming agents in accordance with the purpose. Suitable examples include carbon dioxide-generating compounds, nitrogen gas-generating compounds, oxygen gas-generating compounds, and microcapsule foaming agents. Examples of the carbon dioxide-generating compounds include bicarbonates such as sodium hydrogencarbonate. Examples of the nitrogen gas-generating compounds include a mixture of $NaNO_2$ and $NH_4Cl$; azo compounds such as azobisisobutylonitrile and diazoaminobenzene; and diazonium salts such as p-diazodimethylaniline chloride zinc chloride, morpholinobenzenediazonium chloride zinc chloride, morpholinobenzenediazonium chloride fluoroborate, p-diazoethylaniline chloride zinc chloride, 4-(p-methylbenzoylamino)-2,5-diethoxybenzenediazonium zinc chloride, and sodium 1,2-diazonaphthol-5-sulfonate. Examples of the oxygen gas-generating compounds include peroxides. Examples of the microcapsule foaming agents include microcapsule particulate foaming agents encapsulating low-boiling substances vaporized at low temperatures (which may be liquid or solid at normal temperature). Specific examples of the microcapsule foaming agents include microcapsules 10 to 20 μm in diameter in which low-boiling vaporizable substances such as propane, butane, neopentane, neohexane, isopentane and isobutylene are encapsulated in microcapsules made of polystyrene, polyvinyl chloride, polyvinylidene chloride, polyvinyl acetate, polyacrylate ester, polyacrylonitrile, polybutadiene or any copolymer of these monomers. The content of the foaming agents in the binder resin cannot be specified because it is variable in accordance with the types of the foaming agents. However, it is generally preferable that the content be 1 to 50 wt %.

In the method (I) in which void particles are added, the void volume in the cushioning layer may be adjusted by adding the void particles to, for example, the cushioning layer-forming liquid in such an amount that the void particles will represent 5 to 30 vol % of the whole of the cushioning layer taken as 100 vol %.

In the method (II) utilizing bubbles, the void volume in the cushioning layer may be adjusted by adding the foaming agent to, for example, the cushioning layer-forming liquid in such an amount that the amount of the foaming agent added to the cushioning layer is 1 to 50 vol % relative to the whole of the cushioning layer taken as 100 vol %. In this manner, voids may be introduced into the cushioning layer in the above-mentioned volume ratio relative to the volume of the cushioning layer.

From the point of view of the X-ray transmission properties of the deposition substrates, some or all of the voids are preferably defined by hollow particles.

The reflectance of the deposition substrates may be adjusted by, for example, the following methods.

(1) On the support, a light-shielding layer is provided which is formed of stainless steel or a material including one, or two or more elements selected from aluminum, silver, platinum, palladium, gold, copper, iron, nickel, chromium, and cobalt.

(2) A light-absorbing pigment layer is provided on the support.

(3) A reflective layer, a pigment layer, or a film including at least one of these layers is stacked onto the support.

(4) Light-absorbing properties are imparted to the support.

(5) Light-reflecting properties are imparted to the support.

(6) The cushioning layer is colored.

(7) The content of the light-scattering particles in the cushioning layer is controlled.

(8) At least two of the methods (1) to (7) are combined.

By combining the methods (1) to (7), the reflectance, the absorptance and the transmittance of the inventive deposition substrates with respect to the light (produced in the phosphor layer) may be adjusted freely. Further, the sensitivity of radiographic image detectors may be enhanced by increasing the reflectance of the deposition substrates. By increasing the absorptance of the deposition substrates, radiographic image detectors that include scintillator panels 10 obtained by forming phosphor layers 2 on the deposition substrates according to the present invention may provide radiographic images with improved sharpness. When a metallic light-shielding layer is provided as the aforementioned light-shielding layer and the obtained deposition substrate is used in a scintillator panel 10, advantages are obtained in that because the deposition substrate has a lowered optical transmittance, it becomes possible to prevent the entry of external light or electromagnetic waves through the surface of the support opposite to the surface in contact with the cushioning layer as well as to prevent the leakage of the light produced in the phosphor layer to the outside of the scintillator panel. In particular, the use of a highly reflective metal such as aluminum or silver as the aforementioned light-shielding layer is advantageous in that the reflectance of the cushioning layer including the light-scattering particles and the binder resin can be further increased.

A light-shielding layer including the aforementioned metal material may be formed on surfaces such as the support by any methods without limitation such as deposition, sputtering and metal foil lamination. From the viewpoint of adhesion, sputtering is most preferable.

The cushioning layer itself may be colored with a coloring material by any method without limitation. From points of view such as simplicity, a more preferred method is to add the aforementioned coloring material to the cushioning layer-forming liquid and apply the resultant cushioning layer-forming liquid to the support, thereby forming a colored cushioning layer on the support.

A light-absorbing pigment layer may be provided on the support or a film to be stacked on the support in a similar manner as above. That is, a light-absorbing pigment layer may be formed easily by dispersing or dissolving the aforementioned coloring material and other components such as a binder resin in a solvent, and applying the resultant coating liquid onto the support or the film followed by drying.

At the start of the deposition for the formation of the phosphor layer on the inventive deposition substrate, the volatile content in the cushioning layer is preferably not more than 0.5 mg/m$^2$ relative to the total mass of the cushioning layer. This volatile content ensures that the abnormal growth of columnar phosphor crystals can be prevented.

In the specification, the volatile content is defined by the following equation.

Volatile content (mass %)=$[(M-N)/N] \times 100$

M is the total mass of the cushioning layer before heat treatment, and N is the total mass of the cushioning layer after being heat treated at 200° C. for 3 minutes.

When the volatile content is in the aforementioned range, the release of gas by volatilization from the cushioning layer is reduced during the process in which columnar phosphor crystals are grown by deposition under high temperature and high vacuum conditions. Thus, it becomes possible to suppress the abnormal growth of columnar phosphor crystals in portions from which the volatile components have flown out. Consequently, deteriorations in the sharpness and the uniformity of sharpness in the obtainable radiographic images can be prevented.

If the volatile content in the cushioning layer of the deposition substrate is outside the aforementioned range, the deposition substrate may be subjected to a volatile component removal step to reduce the volatile content in the cushioning layer of the deposition substrate to the above range.

The volatile component removal step is a step in which the volatile components in the cushioning layer of the deposition substrate are removed in vacuum and/or at a high temperature. In the step, any known method may be used as long as the volatile components can be removed. Due to easy operations, a more preferred method is shown in FIG. 3 where the inventive deposition substrate 84 is set to a holder 85 of a deposition apparatus 81, thereafter the holder 85 is heated to 100° C. or above and at the same time the deposition apparatus is evacuated to a vacuum of 100 Pa or less, and the cushioning layer 3 of the deposition substrate is heat treated for several minutes to several hours.

The volatile components are mainly residual solvents that remain in the cushioning layer formed by the application and drying of the cushioning layer-forming liquid, and gases adsorbed to a white pigment used as a raw material. In particular, gases such as vapor ($H_2O$) and carbon dioxide ($CO_2$) are easily adsorbed to the white pigment even in a low humidity environment. Thus, the volatile component removal step is more preferably performed immediately before the phosphor layer 2 is formed by deposition.

(Scintillator Panel Manufacturing Methods)

The scintillator panels of the invention may be manufactured by any methods without limitation as long as the object of the invention is not impaired. Preferably, the scintillator panels are manufactured by a deposition method (a gas-phase deposition method) shown in FIG. 3 which utilizes a deposition apparatus 81 having a deposition source and a rotating mechanism 86 in a vacuum container 82 and which includes a step in which the deposition substrate 84 is set to the rotating mechanism 86 so that the support side of the deposition substrate 84 is in contact with the mounting surface of the rotating mechanism 86, and a phosphor material is deposited onto the scintillator formation scheduled surface of the deposition substrate 84 while rotating the deposition substrate 84 having the support.

A typical example of the methods for manufacturing the inventive scintillator panels will be described with reference to FIGS. 1 to 3. FIG. 1 is a schematic sectional view illustrating a configuration of a scintillator panel 10 as an example of the inventive scintillator panels. FIG. 2 is an enlarged sectional view of the scintillator panel 10 in FIG. 1. FIG. 3 is a schematic view illustrating a configuration of a deposition apparatus 81 as an example of the deposition apparatuses.

The scintillator panels of the invention may be preferably manufactured by a method utilizing the deposition apparatus 81 described in detail below. Hereinafter, a method for manufacturing scintillator panels 10 using the deposition apparatus 81 will be described.

<Deposition Apparatuses>

As illustrated in FIG. 3, the deposition apparatus 81 has a box-shaped vacuum container 82. Near the bottom of the inside of the vacuum container 82, deposition sources 88a and 88b for vacuum deposition are arranged opposite to each other on the circumference of a circle about the central line perpendicular to a deposition substrate 84. The deposition sources 88a and 88b are members into which a deposition material is packed. Electrodes are connected to the deposition sources 88a and 88b. In this case, the gap between the deposition substrate 84 and the deposition sources 88a and 88b is preferably 100 to 1500 mm, and more preferably 200 to 1000 mm. The gap between the central line perpendicular to the deposition substrate 84 and the deposition sources 88a and 88b is preferably 100 to 1500 mm, and more preferably 200 to 1000 mm. The deposition apparatus 81 is configured such that the deposition sources 88a and 88b generate heat by Joule heating by the passage of an electric current through the deposition sources 88a and 88b via the electrodes. In the manufacturing of the scintillator panels 10, a phosphor raw material including cesium iodide and an activator compound is packed in the deposition sources 88a and 88b, and the mixture is heated and vaporized by the passage of an electric current through the deposition sources 88a and 88b. Three or more (for example, eight, sixteen or twenty four) deposition sources 88 may be provided. The deposition sources 88 may be arranged at regular or irregular intervals. The radius of the circle about the central line perpendicular to the deposition substrate 84 may be selected freely.

In order to heat the phosphor contained therein by resistance heating, the deposition sources 88a and 88b may be comprised of alumina crucibles wrapped with a heater, or may be comprised of boats or heaters including high-melting metals or similar materials. The phosphor heating method is not limited to resistance heating and may be any of other methods such as electron beam heating and high frequency induced heating. However, a resistance heating method by the direct application of an electric current, or an indirect resistance heating method by indirect heating of the crucibles with a surrounding heater is preferable because of advantages such as that the method has a relatively simple configuration and is easy to operate, inexpensive and applicable to a very wide range of substances. The deposition sources 88a and 88b may be configured utilizing molecular beam sources according to molecular beam epitaxy.

In the inside of the vacuum container 82, a holder 85 configured to hold the deposition substrate 84 is arranged above the deposition sources 88a and 88b. The holder 85 is provided with a heater (not shown) and is configured to heat the deposition substrate 84 attached to the holder 85 by the operation of the heater. The deposition apparatus 81 is configured, by performing heating of the deposition substrate 84, to detach or remove substances adsorbed to the surface of the deposition substrate 84, to prevent an impurity layer from occurring between the deposition substrate 84 and a phosphor layer formed on the substrate surface, to increase the adhesion between the deposition substrate 84 and the phosphor layer formed on the substrate surface, and to control the quality of the phosphor layer formed on the surface of the deposition substrate 84.

The holder 85 is configured to hold the deposition substrate 84 such that the phosphor layer formation scheduled surface of the deposition substrate 84 is opposed to the bottom of the vacuum container 82 and in parallel to the bottom of the vacuum container 82. The holder 85 is provided with a rotating mechanism 86 capable of rotating the deposition substrate 84 together with the holder 85 in a horizontal direction. The rotating mechanism 86 is comprised of a rotating shaft 87 which supports the holder 85 and rotates the deposition substrate 84, and a motor (not shown) which is arranged outside the vacuum container 82 and serves as a power supply driving the rotating shaft 87. The deposition apparatus 81 is configured such that driving of the motor causes the rotation of the rotating shaft 87 and consequently the rotation of the holder 85 while keeping the holder 85 opposed to the deposition sources 88a and 88b.

Preferably, the holder 85 is fitted with a heater (not shown) for heating the deposition substrate 84. By heating the deposition substrate 84 with the heater, the adhesion of the deposition substrate 84 with respect to the holder 85 can be increased, and the quality of the phosphor layer can be controlled. Such heating also detaches or removes substances which have been adsorbed to the surface of the deposition substrate 84, and prevents an impurity layer from occurring between the surface of the deposition substrate 84 and the phosphor layer. Further, the holder 85 may have a warm or hot medium circulating mechanism (not shown) as a unit for heating the deposition substrate 84. This heating unit is suitable when the temperature of the deposition substrate 84 is maintained at a relatively low temperature such as 50 to 150° C. during the deposition of the phosphor. Furthermore, the holder 85 may have a halogen lamp (not shown) as a unit for heating the deposition substrate 84. This heating element is suited when the temperature of the deposition substrate 84 is maintained at a relatively high temperature such as 150° C. or above during the deposition of the phosphor.

In addition to the above configuration, the deposition apparatus 81 includes a vacuum pump 83 connected to the vacuum container 82. The vacuum pump 83 evacuates the vacuum container 82 and introduces a gas to the inside of the vacuum container 82. The inside of the vacuum container 82 can be maintained in a constant pressure gas atmosphere by the operation of the vacuum pump 83. In order to evacuate the vacuum container 82 to a high vacuum, two or more types of vacuum pumps having different operating pressure ranges may be arranged. Examples of the vacuum pumps include rotary pumps, turbo-molecular pumps, cryogenic pumps, diffusion pumps and mechanical boosters.

The deposition apparatus 81 includes a mechanism configured to introduce a gas into the vacuum container 82 in order to adjust the pressure in the chamber. The gas introduced here is generally an inert gas such as Ne, Ar or Kr. The pressure in the vacuum container 82 may be adjusted by introducing the gas to the desired pressure while evacuating the vacuum container 82 with the vacuum pump 83, or may be adjusted in such a manner that the vacuum container 82 is evacuated to a vacuum lower than the desired pressure, the evacuation is then terminated, and the gas is introduced to the desired pressure. The pressure in the vacuum container 82 may be adjusted by another approach, for example, by providing a pressure control valve between the vacuum container 82 and the vacuum pump 83 so as to adjust the amount of gas evacuated by the pump.

Between the deposition substrate 84 and the deposition sources 88*a* and 88*b*, a shutter 89' is provided which can be opened and closed in a horizontal direction to block the space extending from the deposition sources 88*a* and 88*b* to the deposition substrate 84. The shutter 89' is closed at the initial stage of deposition, whereby even in the event that impurities, if any, which have become attached to the surface of the phosphor contained in the deposition sources 88*a* and 88*b* are vaporized at the initial stage of deposition, the attachment of such impurities to the deposition substrate 84 can be prevented. The shutter 89' is opened after the above purpose is fulfilled, and the phosphor raw material is successfully deposited to form a phosphor layer without allowing any impurities to be deposited to the deposition substrate 84.

(Formation of Phosphor Layers)

The deposition substrate 84 that includes the support and the cushioning layer is set to the holder 85, whilst the deposition sources 88*a* and 88*b* are arranged near the bottom of the vacuum container 82 on the circumference of a circle about the central line perpendicular to the deposition substrate 84. Next, the same number of containers such as crucibles or boats as the deposition sources (two in this case) are filled with a phosphor raw material such as a powdery mixture including a phosphor matrix compound such as cesium iodide and an activator such as thallium iodide, and the filled containers are packed into the deposition sources 88*a* and 88*b* (preparation step). In the case where a phosphor underlayer is formed on the cushioning layer and a phosphor main layer is formed thereafter, the phosphor matrix compound such as cesium iodide and the activator such as thallium iodide may be separately packed into the respective deposition sources. In any of these cases, it is preferable that the gap between the surface of the cushioning layer of the deposition substrate 84 and the deposition sources 88*a* and 88*b* be set to 100 to 1500 mm and the deposition step described later be performed while keeping the gap that has been set.

Where necessary, preliminary heating may be performed prior to the deposition in order to remove impurities in the packed phosphor matrix and activator. The preliminary heating temperature is desirably not more than the melting point of the materials used. For example, the preliminary heating temperature is preferably 50 to 550° C., and more preferably 100 to 500° C. in the case of CsI, and is preferably 50 to 500° C., and more preferably 100 to 500° C. in the case of TlI.

To prevent the impurities from being deposited to the deposition substrate 84, the preliminary heating is preferably performed with the shutter 89 closed.

After the preparation step, the vacuum pump 83 is activated to evacuate the vacuum container 82 and the inside of the vacuum container 82 is brought to a vacuum atmosphere of 0.1 Pa or less (vacuum atmosphere creating step). Here, the term "vacuum atmosphere" refers to an atmosphere in a pressure of not more than 100 Pa, and the vacuum container 82 is preferably evacuated to a vacuum atmosphere in a pressure of not more than 0.1 Pa Thereafter, the inert gas such as Ar is introduced into the vacuum container 82, and the inside of the vacuum container 82 is maintained in a vacuum atmosphere at 0.1 Pa or less. Next, the heater of the holder 85 as well as the motor of the rotating mechanism are driven, and thereby the deposition substrate 84 mounted to the holder 85 is rotated and heated while being opposed to the deposition sources 88*a* and 88*b*. (The rotational speed is variable depending on the size of the apparatus, but is preferably 2 to 15 rpm, and more preferably 4 to 10 rpm.)

Next, the phosphor is deposited. For example, the phosphor such as CsI may be activated by a method in which the phosphor such as CsI and the activator such as a sodium compound, a thallium compound, an indium compound or a europium compound are vaporized simultaneously in the deposition apparatus and are deposited onto the deposition substrate. Particularly, in this method of deposition through the simultaneous vaporization of the phosphor and the activator, the phosphor is preferably CsI from viewpoints such as that the columnar crystal structure provides light guide effects, and the activator compound is preferably an iodide such as sodium iodide (NaI), thallium iodide (TlI) or indium iodide (InI) from viewpoints such as that these iodides do not inhibit the growth of columnar CsI crystals.

Alternatively, the phosphor may be activated by a method in which a phosphor underlayer comprised of columnar crystals of a phosphor such as CsI is deposited onto the deposition substrate 84, thereafter the deposition substrate having the phosphor underlayer is placed in a closed space such as in a deposition apparatus together with an activator compound such as a sodium compound, a thallium compound or an indium compound, and the activator compound is heated to or above its sublimation temperature to activate the phosphor such as CsI while forming a phosphor main layer. In this method in which the substrate having the phosphor layer is heat treated together with the activator, it is preferable that the deposition substrate placed in the closed space, specifically, the phosphor layer formed of the phosphor such as CsI be heated beforehand to a temperature of 100 to 350° C. The phosphor is preferably CsI for reasons such as that the columnar crystal structure thereof provides light guide effects. The activator compound is, although not particularly limited, preferably one having a low sublimation temperature for easy handling. In the above method, CsI may be deposited while being activated with a specific compound (for example, thallium iodide (TlI)). In this manner, the phosphor layer is allowed to contain different kinds of activators between the inside and the surface of the CsI columnar crystals. In this case, in particular, the decay time of the light emitted upon illumination of the phosphor layer may be shortened when a europium compound is used as the activator.

When any phosphor underlayer is not formed on the cushioning layer, an electric current is passed through the deposition sources 88*a* and 88*b* via the electrodes while the deposition substrate 84 is being heated and rotated, and thereby the phosphor raw material such as a mixture including cesium iodide and thallium iodide is vaporized by being heated at about 700° C. to 800° C. for a prescribed time. As a result, a great number of columnar phosphor crystals 2*a* are gradually grown on the surface of the deposition substrate 84, thus forming a phosphor layer 2 with a desired thickness (deposition step). The thickness of the phosphor layer may be variable in accordance with the purpose, but is preferably 120 to 700 μm.

When a phosphor underlayer is to be formed on the cushioning layer, a crucible containing the phosphor matrix compound (such as CsI without activators (pure)) may be heated to allow the phosphor to be deposited to form a phosphor underlayer (a first phosphor layer).

In this process, the temperature of the deposition substrate 84 is usually 5 to 100° C., and preferably 15 to 50° C. The thickness of the phosphor underlayer may be variable depending on the crystal diameters or the thickness of the phosphor layer, but is preferably 0.1 to 50 μm. After the above process, heating of the deposition substrate 84 is initiated to raise the substrate temperature of the deposition substrate 84 to 150 to 250° C., and the operations are started to vaporize the phosphor raw materials including the remaining portion of the phosphor matrix compound (such as CsI without activators (pure)) and the activator (such as TlI). In this process, it is preferable from the point of view of productivity that the phosphor matrix compound be deposited at a higher deposition rate than that in the formation of the underlayer. Although variable depending on the thicknesses of the phosphor underlayer and the phosphor main layer, the rate of this deposition is preferably 5 to 100 times higher, and more preferably 10 to 50 times higher than the rate of the deposition of the phosphor underlayer. The activator may be vaporized in such a manner that the activator alone is vaporized or that a deposition source including a mixture of CsI and TlI is prepared and heated to a temperature (for example, 500° C.) at which TlI alone is vaporized while CsI is not vaporized.

Because the deposition substrate 84 heated during the deposition is hot, its temperature needs to be cooled for the substrate to be removed. In the cooling step, the deposition substrate 84 may be cooled to 80° C. at an average cooling rate in the range of 0.5° C. to 10° C./min. This cooling rate advantageously ensures that the cooling can be performed without causing damages to the deposition substrate 84 due to the thermal shrinkage of the support by quenching. The cooling of the deposition substrate 84 under this condition is particularly effective when, for example, the support in the deposition substrate 84 is a polymer film having a thickness of 50 to 500 μm. In order to avoid any discoloration of the phosphor layer, this cooling step is particularly preferably performed in an atmosphere having a vacuum degree of $1 \times 10^{-5}$ Pa to 0.1 Pa. During the cooling step, an inert gas such as Ar or He may be introduced into the vacuum container of the deposition apparatus. Here, the average cooling rate is determined by continuously measuring the time and the temperature from the start of the cooling (the completion of the deposition) to when the temperature is cooled to 80° C., and calculating the cooling rate per 1 minute.

In the deposition method, reactive deposition may be carried out by introducing a gas such as $O_2$ or $H_2$ as required.

Of the aforementioned columnar phosphor crystal formation methods, the manufacturing method preferably includes a step in which a phosphor underlayer having a higher void content than a phosphor layer is formed on the surface of the substrate, and a step in which the phosphor is deposited by a deposition method on the surface of the phosphor underlayer to form the phosphor main layer. This configuration is preferable in order to satisfy the aforementioned requirement regarding the plane index.

The scintillator panels 10 of the invention may be manufactured in the manner described above.

The aforementioned deposition conditions advantageously ensure that the phosphor layer is formed on the cushioning layer in the form of columnar phosphor crystals grown from the interface thereof with the cushioning layer.

According to the scintillator panel manufacturing method using the deposition apparatus 81, the arrangement of a plurality of deposition sources 88a and 88b allows the vapors from the deposition sources 88a and 88b to be corrected or put in order at their confluence with the result that the crystallinity of the phosphor deposited on the surface of the deposition substrate 84 becomes uniform. Increasing the number of deposition sources increases the number of confluences at which correction occurs, thus resulting in uniform crystallinity of the phosphor over a wider range. By the arrangement of the deposition sources 88a and 88b on the circumference of a circle about the central line perpendicular to the deposition substrate 84, the effects of the correction of vapors providing uniform crystallinity can be obtained isotropically on the surface of the deposition substrate 84.

From the points of view described later, the scintillator panels obtained are preferably subjected to post treatment steps such as the heat treatment step and the pressure treatment step described below.

(Heat Treatment for Phosphor Layers)

Preferably, the phosphor layer formed on the cushioning layer of the deposition substrate is placed in a closed space evacuated to 1.0 Pa or below together with any one activator compound selected from europium iodide and indium iodide, and is subjected to additional activation by heating the activator compound to or above the sublimation temperature to vaporize the compound. By this heat treatment, the emission characteristics of the scintillator layer may be adjusted. In this case, the phosphor such as CsI deposited on the deposition substrate is heated beforehand to a temperature of 250° C. After the additional activation is performed for 1 hour, the deposition substrate having the additionally activated phosphor layer is cooled to 50° C. or below and the scintillator panel is removed from the closed space in the deposition apparatus. In this manner, the phosphor layer in the scintillator panel may be additionally activated. Without the use of any additional activator compounds, the heat treatment alone may be performed for 1 hour in the similar procedures. In this case, the activator that has been added during the deposition is activated, and the scintillator panel achieves a higher emission intensity.

⟨Pressure Treatment for Phosphor Layers⟩

The phosphor layer deposited on the cushioning layer of the inventive deposition substrate is usually a collection of columnar phosphor crystals having a uniform height from the interface thereof with the cushioning layer. However, defects such as the abnormal growth of phosphor crystals occur locally and consequently the phosphor layer has nonuniform heights of the columnar phosphor crystals. For example, such abnormal growth of columnar phosphor crystals may be caused by factors such as dusts, splash during deposition, and substrate defects such as scratches and foreign substances attached to the substrate. Here, the term splash during deposition indicates a phenomenon in which "solids of CsI are scattered before being vaporized and become attached to the deposition substrate" (see, for example, JP-A-2006-335887).

Such abnormally grown columnar phosphor crystals can be a factor that causes a decrease in properties such as sharpness of radiographic images obtained through the scintillator panels. Thus, the pressure treatment described below is performed so that such columnar phosphor crystals are not left as such.

The scintillator panel is pressed to a planar light-receiving element by the application of a pressure from the support side and is thereby brought into close contact (or is bonded) therewith. During this process, the flexible cushioning layer absorbs the irregularities on the surface of the phosphor layer and allows the surface of the phosphor layer to be placed into close contact with the entirety of the light-receiving surface, thus enhancing the uniformity of resolution. FIG. 9 is a schematic view illustrating the phosphor layer being deformed and placed into contact with the planar light-receiving element by the application of a pressure from the support side.

According to the scintillator panel production method of the invention, the cushioning layer is disposed between the support and the phosphor layer. When the scintillator panel is compression bonded to a planar light-receiving element by the application of a pressure to the phosphor layer from the support side, the cushioning layer absorbs irregularities on the phosphor layer and thereby eliminates any gaps in the interface between the planar light-receiving element and the phosphor layer. Thus, it is possible to reduce the occurrence of uneven image densities and the in-plane distribution of MTF in devices such as flat panel detectors.

<Methods for Forming Protective Layers in Scintillator Panels>

A protective layer may be provided in the scintillator panel. The protective layer may be formed by directly coating the surface of the phosphor layer with a protective coating liquid including the aforementioned materials for the protective layer, or may be provided by stacking or bonding via an adhesive a separately prepared protective layer onto the phosphor layer. Alternatively, the materials for the protective layer may be deposited onto the scintillator panel to form the protective layer.

When the protective layer is provided in the inventive scintillator panel, it is preferable to form the protective layer such that the entire surface of the phosphor layer and a portion of the cushioning layer are covered with the continuous protective layer. From viewpoints such as easy production and easy processing of the film, it is particularly preferable that polyparaxylylene be deposited by a chemical vapor deposition (CVD) method to form a polyparaxylylene film as the protective layer on the scintillator panel.

Further, the polyparaxylene film as the protective layer is advantageously formed on the scintillator panel so that the surface roughness (Ra) will be 0.5 to 5.0 µm. In an embodiment in which the scintillator panel is coupled to a planar light-receiving element, this configuration makes it possible to effectively prevent the optical diffusion of light due to regular reflection and total reflection at the interface between the scintillator panel and the planar light-receiving element.

FIG. 8 illustrates an example of the formation of a polyparaxylylene film as the protective layer on the surface of a phosphor layer of a scintillator panel.

A CVD apparatus 50 includes a vaporization chamber 551 into which diparaxylylene that is the raw material for the polyparaxylylene is fed and vaporized, a pyrolysis chamber 552 in which the vaporized diparaxylylene is heated and converted into radicals, a deposition chamber 553 in which the radicals of diparaxylylene are deposited onto the scintillator panel having a scintillator, a cooling chamber 554 for performing deodorization and cooling, and an evacuation system 555 having a vacuum pump. Here, as illustrated in FIG. 8, the deposition chamber 553 has an inlet 553a through which the radicals of diparaxylylene from the pyrolysis chamber 552 are introduced, an outlet 553b through which excess polyparaxylylene is discharged, and a turntable (a deposition table) 553c configured to support the workpiece during the deposition of the polyparaxylylene film.

The scintillator panel is placed on the turntable 553c in the deposition chamber 553 such that the phosphor layer comes upward. Next, the radicals of diparaxylylene generated by vaporization at 175° C. in the vaporization chamber 551 and heating at 690° C. in the Pyrolysis chamber 552 are introduced through the inlet 553a into the deposition chamber 553 and are deposited in a thickness of 2 to 15 µm to form a protective layer (a polyparaxylylene film) 512 for the phosphor layer 2. Here, the inside of the deposition chamber 553 is maintained at a vacuum degree of, for example, 1 to 100 Pa, preferably 13 Pa. The turntable 553c is rotated at a speed of, for example, 0.5 to 20 rpm, preferably 4 rpm. The excess polyparaxylylene is discharged through the outlet 553b to the cooling chamber 554 for performing deodorization and cooling, and the evacuation system 555 having a vacuum pump.

In another embodiment, a hot melt resin may be used as the material for the protective layer. The hot melt resin may also serve as an adhesive for bonding the scintillator panel to the surface of a planar light-receiving element.

The protective layer of a hot melt resin may be formed by any of the following methods which are described as examples.

A release sheet coated with a releasing agent is provided, and a hot melt resin is applied onto the release sheet. The side coated with the hot melt resin is arranged on the surface of the phosphor layer of the scintillator panel, and the layers are bonded to each other under the application of a pressure with a hot roller. After cooling, the release sheet is removed. In another method, the sheet coated with a hot melt resin is arranged on the surface of the phosphor layer, and resin films are arranged on respective other surfaces (meaning not in contact with each other) of the hot melt resin-coated sheet and the phosphor layer. After the peripheral portions of the resin films are sealed (tightly closed) under a reduced pressure, the assembly is heat treated at atmospheric pressure.

In the latter method, the resin films are suitably sealant films or polyethylene terephthalate (PET) dry laminate films. Such films are more advantageous in that uniform bond pressure by atmospheric pressure is obtained in the entire plane of contact between the hot melt resin and the phosphor layer.

When the protective layer is formed on the scintillator panel, a layer including an inorganic substance such as silicon carbide (SiC), silicon dioxide ($SiO_2$), silicon nitride ($Si_3N_4$) or alumina ($Al_2O_3$) may be stacked onto the protective layer by a method such as deposition or sputtering.

Since the performances of the scintillator panels are evaluated with respect to radiographic image apparatuses equipped with units of the scintillator panels and planar light-receiving elements described later, the evaluation of such performances will be discussed in detail after the description of the radiographic image apparatuses.

[Evaluation and Use Applications of Scintillator Panels]

[Radiographic Image Detectors]

⟨Coupling of Scintillator Panels with Planar Light-Receiving Elements⟩

The scintillator panel of the invention should be coupled to a planar light-receiving element by a coupling method which can prevent a decrease in the sharpness of the obtainable radiographic images due to optical diffusion at the joint. In the invention, the scintillator panel is coupled to a planar light-receiving element by bringing the phosphor layer side (the scintillator surface) of the scintillator panel into intimate contact with the surface of the planar light-receiving element by an appropriate pressing technique.

For example, the scintillator panel is coupled to a planar light-receiving element by setting the scintillator panel into a case, arranging sponge sheets to the carbon plate of the radiation incident window and to the radiation incident side (the side without the phosphor layer) of the scintillator panel, and lightly pressing the surface of the scintillator panel and the surface of the planar light-receiving element against each other. That is, the phosphor layer and the planar light-receiving element are bonded together in a pressed condition. Here, the pressure is preferably 0.001% or more of the elastic modulus of the cushioning layer. More preferably, the pressure is such that a light press to the surface of the scintillator panel against the surface of the planar light-receiving element causes the irregularities of the columnar crystals forming the phosphor layer to penetrate into the cushioning layer, specifically, atmospheric pressure.

These problematic deteriorations in the sharpness of radiographic images may be remedied by subjecting the scintillator surface of the scintillator panel and the surface of the planar light-receiving element to an anti-scattering treatment, for example, by providing an anti-optical diffusion layer on the scintillator surface of the scintillator panel, by providing an antireflection layer on at least one of the scintillator surface of the scintillator panel and the surface of the planar light-receiving element, or by controlling the surface roughness (Ra) of either or both of the opposed surfaces, namely, the scintillator surface and the surface of the planar light-receiving element to 0.5 to 5.0 µm. The implementation of the above known coupling method in combination with any of these anti-scattering treatments makes it possible to effectively prevent the scattering of light and to obtain radiographic images with excellent sharpness and excellent uniformity of sharpness.

Here, the anti-optical diffusion layer is a layer which has an optical transmittance of 60 to 99% with respect to 550 nm wavelength light and is disposed on the scintillator panel to serve also as a protective layer. This layer has a function to attenuate the intensity of light propagating through the protective layer.

The antireflection layer prevents a phenomenon in which the light emitted from the scintillator (phosphor layer) of the scintillator panel is repeatedly reflected and propagated between the scintillator surface of the scintillator panel and the surface of the planar light-receiving element, and consequently prevents a failure of the planar light to be detected by the planar light-receiving element. The antireflection layer is a resin layer having a lower refractive index than the scintillator surface when it is disposed on the scintillator surface, and is a resin layer having a lower refractive index than the planar light-receiving element when it is disposed on the surface of the planar light-receiving element. By providing such an antireflection layer on at least one of the scintillator surface of the scintillator panel and the surface of the planar light-receiving element, the emitted light is allowed to be propagated in the antireflection layer at an angle smaller than the angle of incident from the scintillator side and to be propagated to the planar light-receiving element at an angle larger than the above angle, thereby preventing repeated reflection of the emitted light between the scintillator surface and the surface of the planar light-receiving element. More preferably, the antireflection layer is designed such that its optical transmittance with respect to 550 nm wavelength light will be 60 to 99% in order to add effects similar to those obtained with the aforementioned protective layer serving also as the anti-optical diffusion layer.

Further, the surface roughness (Ra) of either or both of the opposed surfaces of the scintillator and of the planar light-receiving element may be advantageously controlled to 0.5 to 5.0 µm. In this manner, the occurrence of regular reflection and total reflection by irregularities on the light incident plane may be suppressed. As a result, it becomes possible to effectively prevent the scintillator light from being diffused between the scintillator surface and the surface of the planar light-receiving element.

More preferably, the same control is applied to the anti-optical diffusion layer and the antireflection layer provided on the scintillator surface or the surface of the planar light-receiving element. Specifically, it is more preferable that the arithmetic surface roughness of their planes (surfaces) placed in contact with the surface of the scintillator panel or the surface of the planar light-receiving element be controlled to 0.5 to 5.0 µm. In this manner, combined effects in the prevention of optical diffusion may be obtained.

Examples of the anti-optical diffusion layers and the antireflection layers include layers containing materials such as polyparaxylylenes, polyurethanes, vinyl chloride copolymers, vinyl chloride.vinyl acetate copolymers, vinyl chloride.vinylidene chloride copolymers, vinyl chloride.acrylonitrile copolymers, butadiene acrylonitrile copolymers, polyamide resins, polyvinyl butyrals, polyester resins, cellulose derivatives (such as nitrocellulose), styrene.butadiene copolymers, various synthetic rubber resins, phenolic resins, epoxy resins, urea resins, melamine resins, phenoxy resins, silicone resins, acrylic resins and urea.formamide resins. These materials may be used singly, or two or more may be mixed together. The anti-optical diffusion layer and the antireflection layer are preferably polyparaxylylene films formed by, in particular, a chemical vapor deposition (CVD) method from viewpoints such as that such layers may be easily formed on the scintillator surface of the scintillator panel or the surface of the planar light-receiving element, and that such layers also have a function as protective layers for the scintillator. In this case, a separate protective layer is not necessarily provided because the polyparaxylylene film serves as a protective layer, an anti-optical diffusion layer and an antireflection layer.

When the optical transmittance of the anti-optical diffusion layer is adjusted by the addition of a coloring material, a blue coloring material is preferably used from the viewpoint that the blue coloring materials absorb long-wavelength red light which is more prone to scatter than other wavelength light. Examples of the blue coloring materials include ultramarine blue, Prussian blue (iron ferrocyanide), phthalocyanine, anthraquinone, indigoid and carbonium.

⟨Radiographic Image Detectors Including Imaging Panels Incorporating Scintillator Panels Coupled with Planar Light-Receiving Elements⟩

Hereinbelow, an example of the applications of the inventive scintillator panels will be described with reference to FIGS. 4 and 5 illustrating a configuration of a radiographic image detector 100 equipped with the scintillator panel 10.

In the radiographic image detector 100, the scintillator panel coupled with a planar light-receiving element is incorporated in an imaging panel.

FIG. 4 is a partially broken schematic perspective view illustrating a configuration of the radiographic image detector 100. FIG. 5 is an enlarged sectional view of the imaging panel 51.

As illustrated in FIG. 4, the radiographic image detector 100 includes the imaging panel 51, a control section 52 configured to control the operations of the radiographic image detector 100, a memory section 53 configured to store image signals output from the imaging panel 51 in a medium such as a rewritable special memory (for example, a flash memory), and a power supply section 54 that supplies electrical power required to drive the imaging panel 51 and to acquire image signals. These and other components are accommodated in a housing 55. The housing 55 is provided with a communication connector 56 for establishing a communication between the radiographic image detector 100 and an external device as required, an operation section 57 for switching the operations of the radiographic image detector 100, and a display section 58 configured to display messages such as that the radiographic image detector is ready for imaging, or that the memory section 53 has stored a predetermined volume of image signals.

The radiographic image detector 100 including the power supply section 54 and the memory section 53 capable of storing radiographic image signals may be detachably connected via the connector 56 to a computer to which the images will be forwarded. According to this configuration, the radiographic image detector 100 does not have to be located at a fixed position with the computer and may be transported from one place to another.

As illustrated in FIG. 5, the imaging panel 51 includes the scintillator panel 10, and an output substrate 20 that absorbs electromagnetic waves from the scintillator panel 10 and outputs the image signals.

In the imaging panel 51, the scintillator panel 10 is arranged on the radiation-illuminated side so that the phosphor layer is in contact with the light-receiving element, and is configured to emit electromagnetic waves corresponding to the intensities of the incident radiations.

The output substrate 20 is disposed opposite to the radiation-illuminated side of the scintillator panel 10, and includes a separator film 20*a*, the planar light-receiving element 20*b*, an image signal output layer 20*c*, and a base 20*d* sequentially in the order of increasing distance from the scintillator panel 10.

The separator film 20*a* separates the scintillator panel 10 and the adjacent layers (in the imaging panel 51, the output substrate 20).

The planar light-receiving element 20*b* includes a transparent electrode 21, a charge generation layer 22 that generates electric charges by being excited by the electromagnetic waves incident thereon through the transparent electrode 21, and a counter electrode 23 that makes a pair with the transparent electrode 21. These are disposed in the order of the transparent electrode 21, the charge generation layer 22 and the counter electrode 23 as viewed from the separator film 20*a* side.

The transparent electrode 21 is capable of transmitting electromagnetic waves which are to be photoelectric converted and is made of, for example, a conductive transparent material such as indium tin oxide (ITO), tin (IV) oxide ($SnO_2$) or zinc oxide (ZnO).

The charge generation layer 22 is disposed in the form of a thin film on the surface of the transparent electrode 21 opposite to the surface in contact with the separator film 20*a*. The charge generation layer 22 includes photoelectric conversion compounds, namely, organic compounds that undergo charge separation when illuminated with light. The organic compounds which produce charge separation are a conductive compound serving as an electron donor by donating electric charges, and another conductive compound serving as an electron acceptor. When electromagnetic waves such as radiations are incident on the charge generation layer 22, the electron donor is excited to release electrons, and the released electrons are transferred to the electron acceptor. In this manner, charges, namely, hole and electron carriers are generated in the charge generation layer 22.

Examples of the conductive compounds as the electron donors include p-type conductive polymer compounds. Preferred p-type conductive polymer compounds are those compounds having a basic skeleton of polyphenylene vinylene, polythiophene, poly(thiophene vinylene), polyacetylene, polypyrrole, polyfluorene, poly(p-phenylene) or polyaniline.

Examples of the conductive compounds as the electron acceptors include n-type conductive polymer compounds. Preferred n-type conductive polymer compounds are those compounds having a basic skeleton of polypyridine, and particularly preferred compounds are those having a basic skeleton of poly(p-pyridyl vinylene).

The thickness of the charge generation layer 22 is preferably not less than 10 nm, and particularly preferably not less than 100 nm in order to ensure a sufficient amount of optical absorption, and is preferably not more than 1 µm, and particularly preferably not more than 300 nm in order to avoid an excessively high electric resistance.

The counter electrode 23 is disposed on the surface of the charge generation layer 22 opposite to the surface on which the electromagnetic waves (the light emitted from the phosphor layer 2 of the scintillator panel 10) are incident. For example, the counter electrode 23 may be selected from general metal electrodes such as gold, silver, aluminum and chromium as well as from transparent electrodes similar to the transparent electrode 21. In order to achieve good characteristics, the electrode is preferably formed from a material with a low work function (not more than 4.5 eV) selected from metals, alloys, electrical conductive compounds and mixtures of these substances.

Between the charge generation layer 22 and each of the electrodes (the transparent electrode 21 and the counter electrode 23), a buffer layer may be disposed which serves as a buffer zone preventing the reaction between the charge generation layer 22 and the electrodes. For example, the buffer layers may be formed using lithium fluoride, and poly(3,4-ethylenedioxythiophene):poly(4-styrene sulfonate) or 2,9-dimethyl-4,7-diphenyl[1,10]phenanthroline.

The image signal output layer 20*c* stores the charges generated in the planar light-receiving element 20*b*, and outputs signals based on the stored charges. This layer is comprised of capacitors 24 that are charge storage elements for storing the charges generated in the planar light-receiving element 20*b* with respect to each pixel, and transistors 25 that are image signal output elements outputting the stored charges as signals.

Examples of the transistors 25 include TFTs (thin film transistors). The TFTs may be inorganic semiconductor TFTs utilized in devices such as liquid crystal displays or may be organic semiconductor TFTs. TFTs formed on plastic films are preferable. Examples of the TFTs formed on plastic films include amorphous silicon semiconductor TFTs on plastic films, and TFTs obtained by adapting the FSA (fluidic self assembly) technology developed by Alien Technology Corp., USA, specifically, TFTs on flexible plastic films obtained by arranging fine monocrystalline silicon CMOS (Nanoblocks) on embossed plastic films. Further, TFTs including organic semiconductors described in literature such as "Science", 283, 822 (1999), "Appl. Phys. Lett.", 771488 (1998), and "Nature", 403, 521 (2000) may be utilized.

The transistors 25 used in the invention are preferably TFTs fabricated by the FSA technology or organic semiconductor TFTs, and are particularly preferably organic semiconductor TFTs. The fabrication of organic semiconductor TFTs does not entail large facilities such as vacuum deposition apparatuses in contrast to silicon TFTs, and may be accomplished at low costs by utilizing a printing technology or an inkjet technology. Further, organic semiconductor TFTs allow the processing temperature to be decreased, and thus may be formed on heat-labile plastic substrates.

To the transistor 25 are electrically connected the capacitor 24 for storing the charges generated in the planar light-receiving element 20b, and a collector electrode (not shown) serving as one of the electrodes of the capacitor 24. The capacitor 24 stores the charges generated in the planar light-receiving element 20b, and the stored charges are read out by the driving of the transistor 25. That is, the signals of the respective pixels for the radiographic image may be output by the driving of the transistors 25.

The base 20d serves as a support of the imaging panel 51, and may be comprised of a material similar to the support 1.

Next, there will be described the mechanism in which the radiographic image detector 100 detects a radiographic image.

First, the radiographic image detector 100 is illuminated with radiations such as X-rays incident from the scintillator panel 10 side toward the base 20d side of the imaging panel 51.

The radiations incident on the radiographic image detector 100 are absorbed as radiation energy by the phosphor layer 2 of the scintillator panel 10 in the radiographic image detector 100. The radiations are then converted into visible light in the phosphor layer 2, and the visible light (electromagnetic waves) corresponding to the intensities of the radiations is emitted from the phosphor layer 2. A portion of the emitted visible light (electromagnetic waves) enters the output substrate 20 and reaches the charge generation layer 22 through the separator film 20a and the transparent electrode 21 of the output substrate 20. The visible light (electromagnetic waves) is absorbed in the charge generation layer 22, and hole-electron pairs (charge separation) are formed in accordance with the intensities of the absorbed visible light (electromagnetic waves).

The holes and the electrons generated in the charge generation layer 22 are transported to the respective electrodes (the transparent electrode 21 and the counter electrode 23) by the action of an internal electric field produced by the application of bias voltage from the power supply section 54, resulting in the passage of photocurrent.

The holes transported to the counter electrode 23 side are stored in the capacitors 24 of the image signal output layer 20c. When the transistors 25 connected to the capacitors 24 are driven, the stored holes are output as image signals, which are then stored in the memory section 53.

Because of the incorporation of the radiographic scintillator panel 10, the radiographic image detector 100 achieves a high photoelectric conversion efficiency and an improved S/N ratio during low-dose imaging of radiographic images, and can reduce image unevenness and linear noise.

[Method for Evaluating Performances of Scintillator Panels]
<Method for Evaluating Sharpness of Scintillator Panel>

With an X-ray illuminator having a tube voltage of 80 kVp, X-rays are applied to the backside (the surface without the phosphor layer) of the scintillator panel through a lead MTF chart, and the image data detected at a CMOS flat panel is recorded on a hard disk. Thereafter, the image data recorded on the hard disk is analyzed with a computer to determine the MTF value (at a spatial frequency of 1 cycle/mm) of the X-ray image recorded on the hard disk, as the indicator of sharpness. A larger value of MTF, which is an abbreviation for modulation transfer function, indicates higher sharpness of the X-ray image.

The present invention will be described in detail by presenting examples hereinbelow without limiting the scope of the invention.

Comparative Example 1

(Fabrication of Deposition Substrate I)

With a 125 μm thick polyimide film (UPILEX-125S manufactured by UBE INDUSTRIES, LTD.) as a support, a deposition substrate I was formed by the following procedures.

10 Parts by mass of a polyester resin (VYLON GK140 manufactured by TOYOBO CO., LTD.), and 40 parts by mass of cyclohexanone and 40 parts by mass of methyl ethyl ketone (MEK) as solvents were mixed together. The mixture was dispersed with a sand mill to give a cushioning layer-forming liquid. The cushioning layer-forming liquid was applied onto the polyimide film support 500 mm in width with a comma coater. The cushioning layer-forming liquid was dried at 180° C. for 3 minutes to form a resin layer on the support. In this manner, a deposition substrate I including the support and the cushioning layer was fabricated.

(Fabrication of Scintillator Panel)

A phosphor (CsI:TlI (0.3 mol %)) was deposited onto the cushioning layer of the deposition substrate I with use of a deposition apparatus illustrated in FIG. 3. A phosphor layer was thus formed.

Specifically, first, the phosphor as the deposition material was packed into a resistance-heating crucible. Further, the support side of the deposition substrate I was set to the rotatable holder 85 and the gap between the deposition substrate I and the deposition source was adjusted to 400 mm.

Next, the deposition apparatus was evacuated, and the degree of vacuum was adjusted to 0.5 Pa by introducing Ar gas. While rotating the deposition substrate I at 10 rpm, the temperature of the deposition substrate I was maintained at 150° C. Next, the resistance-heating crucible was heated to allow the phosphor to be deposited. The deposition was terminated when the thickness of the phosphor layer reached 50 μm. In this manner, a scintillator panel described in Table 1 was obtained.

Examples 1 to 3

Scintillator panels described in Table 1 were fabricated in the same manner as in COMPARATIVE EXAMPLE 1, except that the thickness of the cushioning layer in COMPARATIVE EXAMPLE 1 was changed as described in Table 1.

Comparative Example 2

A scintillator panel described in Table 1 was fabricated in the same manner as in EXAMPLE 2, except that the difference between the largest value and the smallest value of the thickness of the phosphor layer in EXAMPLE 2 was changed as described in Table 1.

Comparative Example 3

(Fabrication of Deposition Substrate II)

With a 125 μm thick polyimide film (UPILEX-125S manufactured by UBE INDUSTRIES, LTD.) as a support, a deposition substrate II was formed by the following procedures.

A mixture was prepared by mixing 40 parts by mass of a combination of a polyester resin (VYLON GK140 manufactured by TOYOBO CO., LTD.) as a binder resin and rutile-form titanium dioxide as light-scattering particles (CR93 manufactured by ISHIHARA SANGYO KAISHA, LTD., average particle diameter 0.28 μm) in a volume ratio of 80:20, and 30 parts by mass of cyclohexanone and 30 parts by mass of methyl ethyl ketone (MEK) as solvents. The mixture was dispersed with a sand mill to give a cushioning layer-forming liquid. The cushioning layer-forming liquid was applied onto the polyimide film support 500 mm in width with a comma coater. The cushioning layer-forming liquid was dried at 180° C. for 3 minutes to form a resin layer on the support. In this manner, a deposition substrate II including the support and the cushioning layer was fabricated.
(Fabrication of Scintillator Panel)

A scintillator panel described in Table 1 was fabricated in the same manner as in COMPARATIVE EXAMPLE 1, except that the formulation of the cushioning layer in COMPARATIVE EXAMPLE 1 was changed to the one described above.

Examples 4 to 6

Scintillator panels described in Table 1 were fabricated in the same manner as in COMPARATIVE EXAMPLE 3, except that the thickness of the cushioning layer in COMPARATIVE EXAMPLE 3 was changed as described in Table 1.

Examples 7 and 8

Scintillator panels described in Table 1 were fabricated in the same manner as in EXAMPLE 5, except that the ratio of the resin to the light-scattering particles in the cushioning layer in EXAMPLE 5 was changed as described in Table 1.

Example 9

A scintillator panel described in Table 1 was fabricated in the same manner as in EXAMPLE 5, except that the resin in the cushioning layer and the ratio of the resin to the light-scattering particles in the cushioning layer in EXAMPLE 5 were changed as described in Table 1.

Comparative Example 4

(Fabrication of Deposition Substrate III)

A 500 μm thick support made of amorphous carbon (manufactured by Nisshinbo Holdings Inc.) was placed into a deposition chamber of a CVD apparatus and was exposed to a vapor produced by sublimating polyparaxylylene (PARYLENE C) as the raw material. In this manner, a deposition substrate III was obtained in which the surface of the phosphor layer was coated with the polyparaxylylene resin film with a thickness of 10 μm.
(Fabrication of Scintillator Panel)

A scintillator panel described in Table 1 was fabricated in the same manner as in COMPARATIVE EXAMPLE 1, except that the formulations and the thicknesses of the support and the cushioning layer in COMPARATIVE EXAMPLE 1 were changed to those described above.

Example 10

A scintillator panel described in Table 1 was fabricated in the same manner as in COMPARATIVE EXAMPLE 4, except that the difference between the largest value and the smallest value of the thickness of the phosphor layer in COMPARATIVE EXAMPLE 4 was changed as described in Table 1.

Example 11

A scintillator panel described in Table 1 was fabricated in the same manner as in EXAMPLE 10, except that the support in EXAMPLE 10 was changed to aluminum having a thickness of 500 μm.

Example 12

A scintillator panel described in Table 1 was fabricated in the same manner as in EXAMPLE 5, except that aluminum as a conductive layer was deposited in a thickness of 0.1 nm onto the surface of the support (between the support and the cushioning layer) in EXAMPLE 5.

Example 13

A scintillator panel described in Table 1 was fabricated in the same manner as in EXAMPLE 5, except that aluminum as a conductive layer was deposited in a thickness of 0.1 nm onto the backside of the support (onto the surface opposite to the phosphor layer) in EXAMPLE 5.

Example 14

A scintillator panel described in Table 1 was fabricated in the same manner as in EXAMPLE 5, except that a polyethylene dioxythiophene (PEDOT) dispersion (manufactured by KAKEN INDUSTRY CO., LTD.) was applied to the backside of the support (to the surface opposite to the phosphor layer) in EXAMPLE 5 so that the dry thickness would be 1 μm.
Evaluation of Scintillator Panels The obtained test pieces were each set to a CMOS flat panel (X-ray CMOS camera system Shad-o-Box 4KEV manufactured by Teledyne Rad-icon Imaging Corporation). With the obtained 12 bit output data, the sharpness of the X-ray image obtained via the scintillator flat panel was measured by the following method. The measured sharpness was evaluated by the method described below.

Sponge sheets were applied to the carbon plate of the radiation incident window of the CMOS flat panel as well as to the radiation incident side (the side without the scintillator layer) of the scintillator panel, and the surface of the scintillator panel and the surface of the planar light-receiving element disposed in the CMOS flat panel were pressed against each other to fix the scintillator panel to the planar light-receiving element.
(Method for Evaluating Unevenness in Images Obtained via Scintillator Panels)

Without the application of X-rays to the flat panel, an iron ball weighing 100 g was dropped from a height of 50 mm onto the carbon plate, thereby applying vibrations to the flat panel. The performance was evaluated as acceptable when the difference between the largest value and the smallest value of the signals in the plane of the dark image obtained was within 10% of the in-plane average of the signals obtained in the absence of loads.
(Method for Evaluating Sharpness of Scintillator Panel)

With an X-ray illuminator having a tube voltage of 80 kVp, X-rays were applied to the backside (the surface without the phosphor layer) of the scintillator panel through a lead MTF chart, and the image data detected at the CMOS flat panel was recorded on a hard disk. Thereafter, the image data recorded on the hard disk was analyzed with a computer to determine the MTF value (at a spatial frequency of 1 cycle/mm) of the X-ray image recorded on the hard disk, as the indicator of sharpness. A larger value of MTF, which is an abbreviation for modulation transfer function, indicates higher sharpness of the X-ray image.

83: VACUUM PUMP
84: DEPOSITION SUBSTRATE
85: HOLDER

TABLE 1

| | Scintillator configurations | | | | | | |
|---|---|---|---|---|---|---|---|
| | Phosphor layer | | | Cushioning layer | | | |
| | In-plane difference in thickness (Largest value − Smallest value) μm | Support | | | Light-scattering particles | Resin/Light-scattering particles ratio vol %/vol % | Elastic modulus GPa |
| | | Materials | Thickness μm | Resins | | | |
| Comp. Ex. 1 | 20 | Polyimide | 125 | VYLON GK140 | — | 100/0 | 0.25 |
| Ex. 1 | 20 | Polyimide | 125 | VYLON GK140 | — | 100/0 | 0.25 |
| Ex. 2 | 20 | Polyimide | 125 | VYLON GK140 | — | 100/0 | 0.25 |
| Ex. 3 | 20 | Polyimide | 125 | VYLON GK140 | — | 100/0 | 0.25 |
| Comp. Ex. 2 | 60 | Polyimide | 125 | VYLON GK140 | — | 100/0 | 0.25 |
| Comp. Ex. 3 | 20 | Polyimide | 125 | VYLON GK140 | $TiO_2$ | 80/20 | 0.4 |
| Ex. 4 | 20 | Polyimide | 125 | VYLON GK140 | $TiO_2$ | 80/20 | 0.4 |
| Ex. 5 | 20 | Polyimide | 125 | VYLON GK140 | $TiO_2$ | 80/20 | 0.4 |
| Ex. 6 | 20 | Polyimide | 125 | VYLON GK140 | $TiO_2$ | 80/20 | 0.4 |
| Ex. 7 | 20 | Polyimide | 125 | VYLON GK140 | $TiO_2$ | 40/60 | 2.5 |
| Ex. 8 | 20 | Polyimide | 125 | VYLON GK140 | $TiO_2$ | 20/80 | 12 |
| Ex. 9 | 20 | Polyimide | 125 | VYLON 550 | $TiO_2$ | 20/80 | 7 |
| Comp. Ex. 4 | 20 | Amorphous carbon | 500 | PARYLENE C | — | — | 2.4 |
| Ex. 10 | 5 | Amorphous carbon | 500 | PARYLENE C | — | — | 2.4 |
| Ex. 11 | 5 | Aluminum | 500 | PARYLENE C | — | — | 2.4 |
| Ex. 12 | 20 | Polyimide | 125 | VYLON GK140 | $TiO_2$ | 80/20 | 0.4 |
| Ex. 13 | 20 | Polyimide | 125 | VYLON GK140 | $TiO_2$ | 80/20 | 0.4 |
| Ex. 14 | 20 | Polyimide | 125 | VYLON GK140 | $TiO_2$ | 80/20 | 0.4 |

| | Scintillator configurations | | | Evaluation results | | |
|---|---|---|---|---|---|---|
| | Cushioning layer | | Conductive layer | | Evaluations | |
| | Thickness μm | Thickness of cushioning layer/In-plane difference in thickness | Materials | Surface specific resistance Ω/□ | Image unevenness | Sharpness |
| Comp. Ex. 1 | 5 | 0.3 | — | $1 \times 10^{12}$ | 18 | 0.62 |
| Ex. 1 | 25 | 1.3 | — | $1 \times 10^{12}$ | 8 | 0.58 |
| Ex. 2 | 50 | 2.5 | — | $1 \times 10^{12}$ | 6 | 0.55 |
| Ex. 3 | 250 | 12.5 | — | $1 \times 10^{12}$ | 5 | 0.48 |
| Comp. Ex. 2 | 50 | 0.8 | — | $1 \times 10^{12}$ | 12 | 0.55 |
| Comp. Ex. 3 | 5 | 0.3 | — | $1 \times 10^{12}$ | 14 | 0.67 |
| Ex. 4 | 25 | 1.3 | — | $1 \times 10^{12}$ | 5 | 0.68 |
| Ex. 5 | 50 | 2.5 | — | $1 \times 10^{12}$ | 3 | 0.66 |
| Ex. 6 | 250 | 12.5 | — | $1 \times 10^{12}$ | 3 | 0.63 |
| Ex. 7 | 50 | 2.5 | — | $1 \times 10^{12}$ | 5 | 0.67 |
| Ex. 8 | 50 | 2.5 | — | $1 \times 10^{12}$ | 8 | 0.66 |
| Ex. 9 | 50 | 2.5 | — | $1 \times 10^{12}$ | 5 | 0.66 |
| Comp. Ex. 4 | 10 | 0.5 | — | $1 \times 10^{6}$ | 15 | 0.32 |
| Ex. 10 | 10 | 2.0 | — | $1 \times 10^{6}$ | 8 | 0.62 |
| Ex. 11 | 10 | 2.0 | — | 1.5 | 6 | 0.58 |
| Ex. 12 | 50 | 2.5 | Al (front side) | 1.5 | 2 | 0.68 |
| Ex. 13 | 50 | 2.5 | Al (backside) | 1.5 | 2 | 0.68 |
| Ex. 14 | 50 | 2.5 | PEDOT (backside) | 120 | 3 | 0.68 |

VYLON 550 and VYLON GK140: Amorphous polyester resins manufactured by TOYOBO CO., LTD.

REFERENCE SIGNS LIST

10: SCINTILLATOR PANEL
1: SUPPORT
1': SUPPORT
2: PHOSPHOR LAYER
2a: COLUMNAR PHOSPHOR CRYSTAL
3: CUSHIONING LAYER
4: UNDERCOAT LAYER
61: CENTRAL LINE
62: LIGHT-SCATTERING PARTICLE
63: BINDER RESIN
81: DEPOSITION APPARATUS
82: VACUUM CONTAINER
76: ROTATING MECHANISM
87: ROTATING SHAFT
88 (88a, 88b): DEPOSITION SOURCE
89': SHUTTER
29: FEED STEP
39: APPLICATION STEP
49: DRYING STEP
59: HEAT TREATMENT STEP
69: RECOVERY STEP
89: DRYING STEP
109: PRODUCTION APPARATUS
202: ROLL OF SUPPORT WOUND AROUND CORE
301: BACKUP ROLL
302: APPLICATION HEAD

303: VACUUM CHAMBER
304: APPLICATOR
401: DRYER
402: INLET
403: OUTLET
801: DRYER
802: INLET
803: OUTLET
501: HEAT TREATMENT APPARATUS
502: HEAT TREATMENT GAS INLET
503: OUTLET
601: RECOVERED ROLL OF SUPPORT WOUND AROUND CORE
a: CONVEYOR ROLL
b: CONVEYOR ROLL
c: CONVEYOR ROLL
d: CONVEYOR ROLL
50: DEPOSITION APPARATUS
551: VAPORIZATION CHAMBER
552: PYROLYSIS CHAMBER
553: DEPOSITION CHAMBER
553a: INLET
553b: OUTLET
553c: TURNTABLE (DEPOSITION TABLE)
554: COOLING CHAMBER
555: EVACUATION SYSTEM
512: DEPOSITION OF PROTECTIVE LAYER (POLYP XYLENE FILM)
100: RADIOGRAPHIC IMAGE DETECTOR
51: IMAGING PANEL
52: CONTROL SECTION
53: MEMORY SECTION
54: POWER SUPPLY SECTION
55: HOUSING
56: CONNECTOR
57: OPERATION SECTION
58: DISPLAY SECTION
20: OUTPUT SUBSTRATE
20a: SEPARATOR FILM
20h: PLANAR LIGHT-RECEIVING ELEMENT
20c: IMAGE SIGNAL OUTPUT LAYER
20d: BASE
21: TRANSPARENT ELECTRODE
22: CHARGE GENERATION LAYER
23: COUNTER ELECTRODE
24: CAPACITOR
25: TRANSISTOR

The invention claimed is:

1. A scintillator panel comprising, in the order named, a support, a cushioning layer disposed on a surface of the support, and a phosphor layer comprising columnar crystals deposited on a surface of the cushioning layer,
the cushioning layer having a thickness larger than the difference between the largest value and the smallest value of the thickness of the columnar crystals of the phosphor layer deposited on the surface of the cushioning layer,
the phosphor layer being configured to be placed into uniform contact with a surface of a planar light-receiving element when the phosphor layer is pressed against the planar light-receiving element by the application of a pressure from the support side through the cushioning layer,
wherein the cushioning layer has a thickness in a range of 10 to 250 µm, and
wherein the phosphor layer comprises:
a phosphor underlayer; and
a phosphor main layer formed on the phosphor under layer,
wherein the phosphor underlayer has a lower void content than the phosphor main layer.

2. The scintillator panel according to claim 1, wherein the cushioning layer includes light-reflecting particles or light-absorbing particles.

3. The scintillator panel according to claim 2, wherein the light-reflecting particles include at least titanium dioxide.

4. The scintillator panel according to claim 1, wherein the scintillator panel has electric conductivity.

5. The scintillator panel according to claim 1, wherein the support is based on a resin.

6. A method for producing a scintillator panel comprising:
forming a cushioning layer on a surface of a support; and
forming a phosphor layer comprising columnar crystals on a surface of the cushioning layer by a deposition method,
wherein the cushioning layer being formed on the support so as to have a thickness enough to surpass a difference expected between the largest value and the smallest value of the thickness of the columnar crystals of the phosphor layer deposited on the surface of the cushioning support,
the phosphor layer being formed on the cushioning layer so that the phosphor layer is allowed to be placed into uniform contact with a surface of a planar light-receiving element when the phosphor layer is pressed against the planar light-receiving element by the application of a pressure from the support side through the cushioning layer,
wherein the cushioning layer has a thickness in a range of 10 to 250 µm, and
wherein the phosphor layer comprises:
a phosphor underlayer; and
a phosphor main layer formed on the phosphor under layer,
wherein the phosphor underlayer has a lower void content than the phosphor main layer.

7. The scintillator panel production method according to claim 6, wherein the cushioning layer includes light-reflecting particles or light-absorbing particles.

8. The scintillator panel production method according to claim 7, wherein the light-reflecting particles include at least titanium dioxide.

9. The scintillator panel production method according claim 6, wherein the scintillator panel has electric conductivity.

10. The scintillator panel production method according to claim 6, wherein the support is based on a resin.

* * * * *